(12) United States Patent
Baranowski et al.

(10) Patent No.: US 10,099,842 B2
(45) Date of Patent: Oct. 16, 2018

(54) PRODUCT DISPENSING SYSTEM

(71) Applicant: S.C. JOHNSON & SON, INC., Racine, WI (US)

(72) Inventors: Brad P. Baranowski, Racine, WI (US); David C. Belongia, Burlington, WI (US); Scott D. Walter, Twin Lakes, WI (US); Aparna Unnikrishnan, Evanston, IL (US)

(73) Assignee: S.C. JOHNSON & SON, INC., Racine, WI (US)

( * ) Notice: Subject to any disclaimer, the term of this patent is extended or adjusted under 35 U.S.C. 154(b) by 0 days.

(21) Appl. No.: 14/980,380

(22) Filed: Dec. 28, 2015

(65) Prior Publication Data
US 2016/0130072 A1 May 12, 2016

Related U.S. Application Data

(63) Continuation of application No. 13/607,583, filed on Sep. 7, 2012, now Pat. No. 9,247,724.

(51) Int. Cl.
*B67D 7/06* (2010.01)
*B65D 83/26* (2006.01)
(Continued)

(52) U.S. Cl.
CPC ......... *B65D 83/262* (2013.01); *A01M 1/2038* (2013.01); *A61L 9/12* (2013.01);
(Continued)

(58) Field of Classification Search
CPC ........................... A01M 1/2038; B65D 83/262
(Continued)

(56) References Cited

U.S. PATENT DOCUMENTS 3,101,160 A * 8/1963 Picot .................... B65D 83/384
222/183
3,107,821 A * 10/1963 Lambert ............... B65D 83/262
137/624.13
(Continued)

FOREIGN PATENT DOCUMENTS

EP          2287089 A1    2/2011
FR          1049703 A    12/1953
(Continued)

OTHER PUBLICATIONS

International Search Report and Written Opinion of the International Searching Authority issued in PCT Application No. PCT/US2013/058144, dated May 22, 2014, 18 pages.
(Continued)

*Primary Examiner* — Patrick M Buechner
*Assistant Examiner* — Michael J Melaragno
(74) *Attorney, Agent, or Firm* — Quarles & Brady, LLP

(57) ABSTRACT

A product dispensing system includes a housing that has a sidewall with at least one communication element provided thereon. The sidewall has at least a first side and a second different side coupled to the first side, the first side and the second side each configured to extend below a bottom of a container coupled to the housing. A dispensing opening is provided on a first side of the sidewall. A switch controls an automatic dispensing sequence. The at least one communication element is configured to provide guidance as to how to set-up, hold, orient, spray, or otherwise use the product dispensing system, and the second different side of the sidewall is configured to accommodate a user's hand in an ergonomic manner.

18 Claims, 16 Drawing Sheets

(51) Int. Cl.
  *B65D 83/20* (2006.01)
  *B65D 83/38* (2006.01)
  *A01M 1/20* (2006.01)
  *A61L 9/12* (2006.01)
  *A61L 9/14* (2006.01)

(52) U.S. Cl.
  CPC .............. *A61L 9/14* (2013.01); *B65D 83/20* (2013.01); *B65D 83/206* (2013.01); *B65D 83/384* (2013.01)

(58) Field of Classification Search
  USPC .............................................. 222/183, 402.1
  See application file for complete search history.

(56) References Cited

U.S. PATENT DOCUMENTS

| | | | | |
|---|---|---|---|---|
| 3,195,777 | A * | 7/1965 | Hart | B65D 83/262 222/181.2 |
| 3,508,682 | A * | 4/1970 | Sherman | A47K 5/122 222/145.5 |
| 4,301,946 | A * | 11/1981 | Goldin | F21V 33/0064 200/551 |
| 5,358,147 | A * | 10/1994 | Adams | B65D 83/386 222/183 |
| 5,593,641 | A | 1/1997 | Hornberger, Sr. | |
| 5,904,268 | A * | 5/1999 | Daly | A47G 19/2227 206/457 |
| 6,104,867 | A | 8/2000 | Stathakis et al. | |
| 6,569,387 | B1 * | 5/2003 | Furner | A01M 1/2033 222/183 |
| D604,824 | S * | 11/2009 | Paolazzi | D23/366 |
| 7,643,734 | B2 * | 1/2010 | Wefler | A01M 1/20 392/390 |
| 7,837,065 | B2 * | 11/2010 | Furner | B65D 83/262 222/504 |
| 7,932,482 | B2 * | 4/2011 | Norwood | A01M 1/2077 219/494 |
| 2004/0140328 | A1 | 7/2004 | Pericard et al. | |
| 2005/0023287 | A1 * | 2/2005 | Speckhart | B65D 83/262 222/1 |
| 2007/0199952 | A1 | 8/2007 | Carpenter et al. | |
| 2007/0210105 | A1 * | 9/2007 | Malachowsky | A23G 9/045 222/144.5 |
| 2007/0241134 | A1 | 10/2007 | Gurrisi et al. | |
| 2008/0061082 | A1 * | 3/2008 | Anderson | A61L 9/14 222/183 |
| 2008/0156896 | A1 * | 7/2008 | Anderson | B65D 83/262 239/34 |
| 2008/0277411 | A1 * | 11/2008 | Beland | B65D 83/205 222/52 |
| 2009/0045219 | A1 * | 2/2009 | Helf | A61L 9/14 222/52 |
| 2009/0236362 | A1 * | 9/2009 | Helf | A01M 1/2038 222/52 |
| 2010/0089950 | A1 * | 4/2010 | Helf | B65D 83/206 222/153.09 |
| 2010/0116822 | A1 * | 5/2010 | Perelli | B65F 1/0053 220/4.03 |
| 2010/0140298 | A1 * | 6/2010 | Anderson | A61L 9/12 222/183 |
| 2010/0226818 | A1 * | 9/2010 | Miyagi | A61L 9/048 422/4 |
| 2010/0308076 | A1 * | 12/2010 | Snodgrass | B65D 83/262 222/52 |
| 2011/0036932 | A1 * | 2/2011 | Myoujin | B65D 83/262 239/569 |
| 2011/0057053 | A1 | 3/2011 | Kobayashi et al. | |
| 2011/0192867 | A1 * | 8/2011 | Best | B65D 83/206 222/402.13 |
| 2011/0220682 | A1 * | 9/2011 | Lim | B05B 11/0054 222/183 |
| 2012/0000937 | A1 * | 1/2012 | Cohen | B65D 83/201 222/183 |
| 2012/0091219 | A1 * | 4/2012 | Sipinski | B65D 83/262 239/34 |
| 2012/0118918 | A1 * | 5/2012 | Andersen | B65D 83/201 222/402.13 |
| 2012/0217243 | A1 * | 8/2012 | Cohen | B65D 83/201 220/200 |
| 2013/0032604 | A1 * | 2/2013 | Jamali | B65D 1/40 220/674 |
| 2014/0047983 | A1 * | 2/2014 | Furner | A01M 1/2077 96/301 |
| 2014/0048617 | A1 * | 2/2014 | Furner | A01M 7/0003 239/55 |
| 2014/0061253 | A1 * | 3/2014 | Sweeton | B05B 11/0037 222/382 |
| 2014/0069956 | A1 * | 3/2014 | Baranowski | A61L 9/14 222/183 |
| 2014/0069957 | A1 * | 3/2014 | Baranowski | A01M 1/2038 222/183 |
| 2014/0231449 | A1 * | 8/2014 | Wegelin | B67D 7/346 222/23 |
| 2015/0083755 | A1 * | 3/2015 | Mecker | A61L 9/14 222/183 |

FOREIGN PATENT DOCUMENTS

| | | |
|---|---|---|
| FR | 1303493 A | 9/1962 |
| FR | 2340193 A1 | 9/1977 |
| GB | 2392439 A | 3/2004 |
| WO | 2004/043502 A1 | 5/2004 |
| WO | 2004/044939 A1 | 5/2004 |
| WO | 2006135647 A2 | 12/2006 |
| WO | 2007/120565 A1 | 10/2007 |
| WO | 2008/153678 A2 | 12/2008 |
| WO | 2009/025742 A2 | 2/2009 |

OTHER PUBLICATIONS

Communication pursuant to R. 164(2)(b), § 1 on original claims 8-13 issued in corresponding European Patent Application No. 13763393.9, dated Nov. 2, 2016, 7 pages.

International Search Report and Written Opinion for International Application No. PCT/US2013/058141, dated Feb. 27, 2014, 15 pages.

* cited by examiner

PRODUCT DISPENSING SYSTEM

CROSS REFERENCE TO RELATED APPLICATIONS

This application is a continuation of U.S. non-provisional application Ser. No. 13/607,583, filed Sep. 7, 2012, the contents of which are incorporated herein by reference in their entirety.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates generally to a product dispensing system, and more specifically, to a product dispensing system that is designed to dispense in both manual and automatic actuation modes and that has visual communication elements defined by one or more surface variations.

2. Description of the Background of the Invention

Rooms in homes, businesses and other locations, such as hotels, restaurants, locker rooms, and the like, frequently have an unpleasant or neutral odor that pervades throughout them. The smell of a room is directly tied to the experience that an individual perceives while being located in the room. However, if the home or business employs an automated dispensing system, the dispensing system may disperse the product at times that do not correlate to a user's visit or that do not account for an unexpected olfactory occurrence, e.g., a pet spending time in a room or garbage being left out for an extended period of time. Therefore, it is desirable to have a dispensing device capable of dispersing a product on an automatic basis in the typical course of use while at the same time allowing manual actuation of the dispensing device at appropriate and specifically desired times, e.g., right before a guest visits a home or business.

Bathrooms are particularly challenging rooms for homes and businesses to maintain pleasant odors therein. Bathrooms are a common source of unpleasant odors due to mildew and human waste, and individuals frequently desire to remove the odor and/or mask the unpleasant odor with a more desirable fragrance and/or odor neutralizer. A home or business owner may desire to disperse a pleasant odor through the bathroom on an automated basis, while an individual who uses a bathroom may desire to actuate a dispensing device at some point before, during, or after using the bathroom. Frequently, individuals keep an automatic fragrance device, such as an exposed fragrance gel, in the bathroom that is used to disperse a fragrance automatically on a continuous basis. In contrast, other individuals keep a handheld dispensing device, such as a dispensing device with a trigger, in the bathroom for manual actuation when it is desirable. Further, businesses or other commercial sites typically use large wall mounted devices that only allow for the automatic spraying of fluid. Regrettably, the dispensing devices designed for use in bathrooms are not typically designed to provide automated actuation over an ongoing basis while at the same time allowing for a manual actuation boost on an as-needed basis.

Another common problem facing the rooms of homes and businesses is the controlling of pests, such as mosquitoes, ants, spiders and the like. Individuals frequently place a pest control device in a room with a pest issue and allow the device to disperse an insecticide or other pest-control product on an automated basis. The automation of the device allows pests to be combated even if the individual is not present in the room. On some occasions, individuals encounter pests directly and wish to spray them with the same pest-control dispensing device. Unfortunately, pest control devices typically have not been designed to effectuate both automated actuation and manual actuation to accomplish both goals of an individual eliminating pests by spraying the pest control product directly on or near the pest and having the pest control dispensing device disperse product automatically. Therefore, it would be desirable to have a pest control device that is designed to automatically dispense, but can be easily and comfortably actuated when an individual confronts a pest directly.

Dispensing devices using aerosol containers have been popular and commonly used to store and dispense a product such as air freshening agents, deodorants, insecticides, germicides, decongestants, perfumes, or any other known product. Actuation of an aerosol container typically includes the manual or automatic displacement of a valve stem. In automated dispensing devices, conventional actuator mechanisms may include motor driven linkages that actuate the valve stem to open an aerosol valve within the container. Other actuator mechanisms may include solenoid valves that effect fluid dispensing from aerosol containers when energized. Many types of dispensers such as hand sanitizers, fragrance dispensers, insecticide devices, and the like may utilize any of the aforementioned actuator mechanisms.

Automated actuation systems operably attach to the container and valve stem in various ways. For example, some existing automated actuation systems are contained within a housing unit, which is also adapted to receive the container therein. These types of automated actuation systems may include complicated and large camming mechanisms that require a significant amount of space in the housing, which in turn requires the housing to be larger. Automated actuation systems also typically include at least one button and/or switch that is designed to control the operational parameters of an automated sequence.

Heretofore, dispensing devices have been designed and utilized as either a manual dispensing device or an automated dispensing device, but typically not as both. Automated dispensing devices do not require a user to actuate the valve stem and frequently use a timer, sensor, or other mechanism to control actuation. A drawback of automated devices is habituation by the user to the substance being dispensed and a lack of user control to be able to provide a boost or increase of product as discussed in the various examples provided herein. In other cases, a user may want to increase the fragrance for other reasons, but is unable to provide immediate actuation using a dispensing device designed for automatic actuation. A drawback of manually actuated dispensing devices is that the devices are not capable of operating without human intervention.

Even though some devices are physically capable of being used in both manual and automatic actuation modes, such devices typically are not designed for use in both operating conditions and/or suffer drawbacks related thereto. Some automated dispensing devices have tried to address the aforementioned problem by providing a manual actuation button. However, the manual actuation button has been typically provided on automated dispensing devices in a location that is awkward, confusing, and non-intuitive. In particular, such buttons are typically provided on the inside of a dispensing device or on a portion of the dispensing device, such as a lower third, in a location grasped by the user when the user holds the device (i.e., gripping area) during manual operation thereof. Manual actuation buttons disposed in a gripping area of the device frequently cause inadvertent actuation when a user grasps the dispensing device and accidentally presses the manual actuation button.

An additional obstacle with respect to existing actuation systems is the containment of the actuation mechanisms within bulky and cumbersome housings. Such housings are difficult to grasp and hold, which can lead to the housing being improperly used. For example, the user may inadvertently grasp the housing around an upper portion thereof adjacent an outlet orifice and the user's hand may contact the product during the spraying operation.

Further, manual actuation buttons disposed on the same surface or adjacent to a dispensing orifice of the device presents another challenge. Namely, the user must grasp the device and position her hand around the device to reach the manual actuation button, while at the same time orienting the device outwardly, such that the material is sprayed away from the user through the dispensing orifice. The aforementioned positioning is uncomfortable and awkward for many users. Additionally, due to the non-ergonomic nature of many of the known dispensing devices, users are less likely to hold and use the product on a frequent basis due to hand strain. Still further, women between the ages of 30 and 50 are the most common users of the aforementioned types of dispensing devices and are, on average, able to sustain a gripping force between about 25 N to about 35 N for a time period adequate to hold and spray the dispensing devices disclosed herein. Therefore, it is desirable to provide a dispensing device that is comfortable for the typical user to grasp and hold the dispensing device during use thereof.

Another drawback to existing actuation systems is that the devices may be confusing for the user to operate. In particular, the user may find it difficult or non-intuitive in how to orient the housing properly for spraying. The propensity for improper orientation may be exacerbated in situations where there is a desire to omit written communication elements for orienting the user so as to create an aesthetically pleasing housing that a user will keep out within plain view. A need therefore exists to provide an aesthetically pleasing housing that users will want to keep out in plain sight and that also provides an intuitive means to communicate the proper orientation of the housing to effect proper spraying.

Therefore, it is desirable to have a product dispensing device that overcomes obstacles associated with prior art dispensing devices. In particular, it is desirable to provide a dispensing device that is specifically designed to be used in both a manual actuation mode and an automatic actuation mode. The design elements incorporated into the dispensing device address specific problems as discussed herein. For example, it is advantageous to locate control switches in locations that do not allow accidental actuation of the dispensing device. It is further advantageous to minimize the footprint of the housing of the dispensing system by using a vertically stacked camming mechanism. A smaller housing is not only visually pleasing, it provides for increased ease of actuation and saves money in manufacturing costs.

An additional benefit of the dispensing devices disclosed herein is that they are all-in-one actuation units that are capable of being displayed in a home or business at all times, i.e., always out, because of both the aesthetic qualities of the dispenser and the communication elements provided thereon. In particular, a user can easily grasp and manually actuate the dispenser without leaving the room, even if the dispenser is operating in an automatic dispensing state. The all-in-one aspect of the dispensing device eliminates the need for a user to keep two separate devices in a single room and/or leave the room to search for a separate dispensing device when manual actuation is desired. Use of the dispensing devices disclosed herein also minimizes the number of dispensing devices that a user must keep in their home or business.

The present disclosure provides a further solution to the above problems through the use of one or more non-written communication elements on a housing of a product dispensing device provided in the form of one or more surface variations. The communication element(s) guides the user in proper handling and usage of the device in an intuitive way. In particular, the user should understand how to pick up the device and actuate it, at least in part by using the communication element(s) on the device. The communication element(s) is preferably decorative as well as informative so that the user is able to leave the device out in plain view within a home, office, or other setting. Indeed, the decorative nature of the communication element(s) allows a user to feel comfortable leaving the dispensing device out in the open in a room at all times, which saves a user the extra time and effort of having to obtain an additional dispenser when a different type of dispenser is desired. The present disclosure also provides for an ergonomic housing in which a user's hand can comfortably grasp the housing without significant hand strain.

SUMMARY OF THE INVENTION

According to one aspect of the invention, a product dispensing system includes a housing that has a sidewall with at least one communication element provided thereon, the sidewall having at least a first side and a second different side coupled to the first side, the first side and the second side each configured to extend below a bottom of a container coupled to the housing. A dispensing opening is provided on the first side of the sidewall. A switch controls an automatic dispensing sequence. The at least one communication element is configured to provide guidance as to how to set-up, hold, orient, spray, or otherwise use the product dispensing system, and the second different side of the sidewall is configured to accommodate a user's hand in an ergonomic manner.

According to a different aspect of the invention, a product dispensing system includes a housing having a sidewall extending between a lower surface and an upper surface with at least one communication element thereon, the sidewall including a first side portion coupled to a second side portion that together form a compartment for a container. A dispensing opening is formed completely within the first side portion of the sidewall. The housing is configured to extend below a bottom of the container coupled to the housing. The dispensing opening is provided within an upper region of the housing. The at least one communication element assists the user in avoiding contact with the housing adjacent the dispensing opening to avoid product being dispensed onto the user's hand or to avoid any residual product on the housing adjacent the dispensing opening.

According to a further aspect of the invention, a product dispensing system includes a housing having a sidewall extending between a lower surface and an upper surface with a plurality of communication elements thereon. The sidewall includes a first side portion coupled to an opposing second side portion that together form a compartment for a container. A dispensing opening is formed completely within the first side portion of the sidewall. The dispensing orifice has a shape similar to at least one of the plurality of communication elements. The dispensing orifice is disposed between at least two of the plurality of communication elements on the first side portion.

BRIEF DESCRIPTION OF THE DRAWINGS

Other aspects and advantages of the present invention will become apparent upon consideration of the following detailed description, wherein similar structures have similar reference numerals.

DETAILED DESCRIPTION OF THE DRAWINGS

Figure 1:
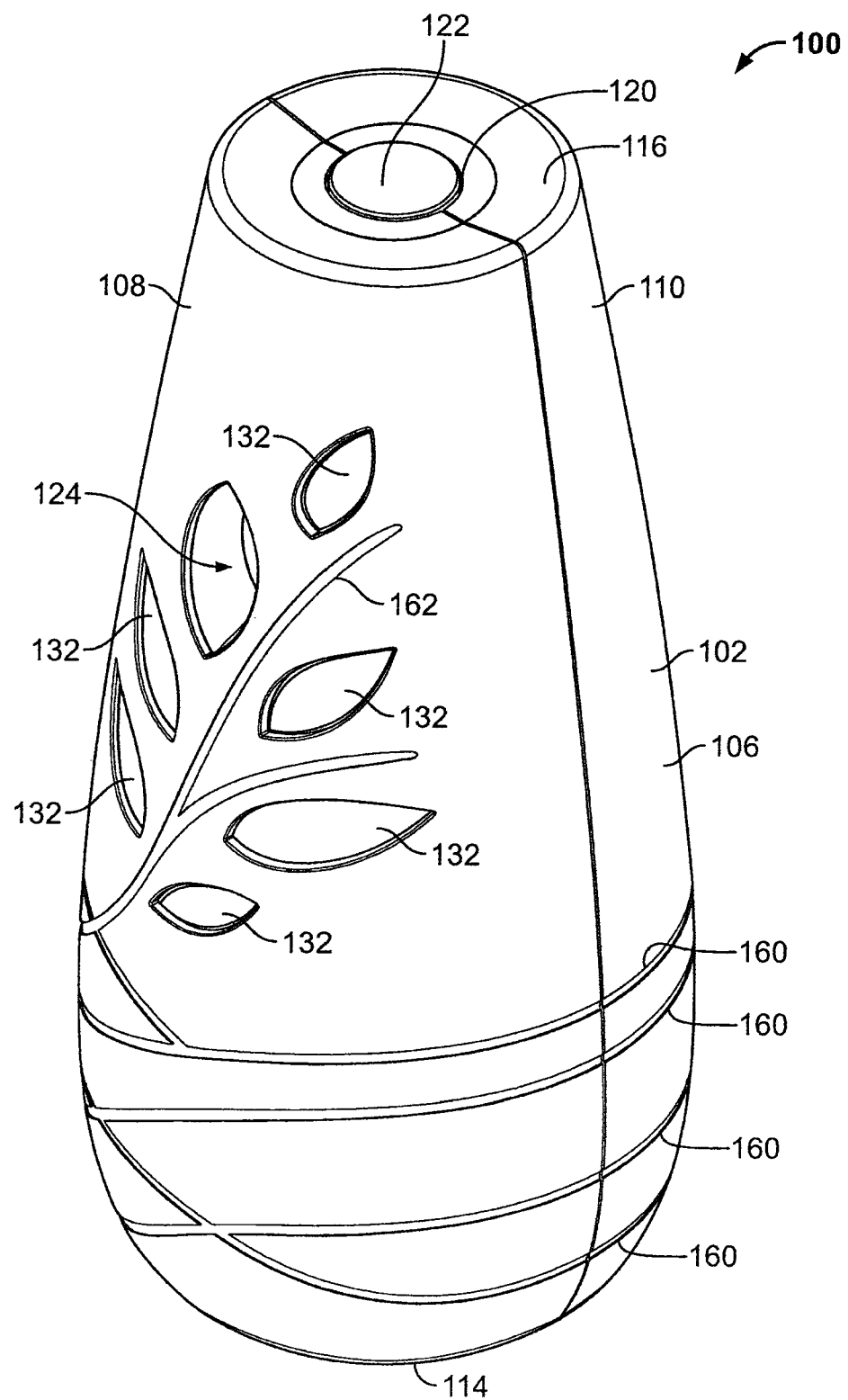
FIG. 1 is a front isometric view of a product dispensing system that includes a housing.

FIGS. 1-19 generally depict a product dispensing system 100 that includes a housing 102 and a container 104 disposed therein. The container 104 includes a product (not shown) that is adapted to be dispensed into the atmosphere. The housing 102 has a substantially solid sidewall 106 comprising a semi-circular front portion 108 that is attached to a similarly shaped rear portion 110. The front portion 108 and rear portion 110 form a compartment 112 that encloses and holds the container 104 in an upright position. The housing 102 may be opened to insert and/or remove the container 104 from the housing 102 prior to and after use, as will be explained in more detail below.

Figure 2:
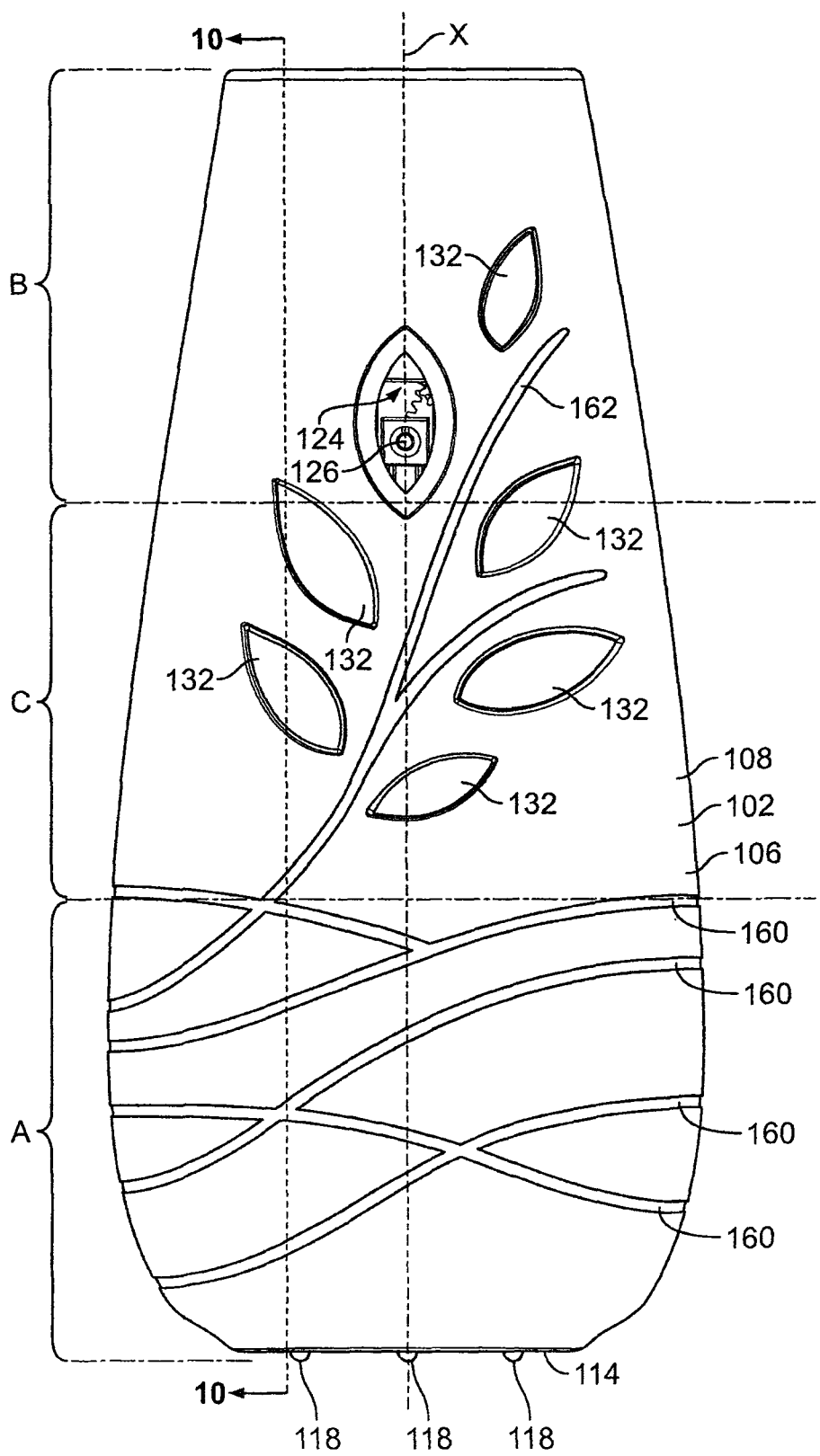
FIG. 2 is a front elevational view of the product dispensing system of FIG. 1.

The sidewall 106 of the housing 102 extends upwardly from a substantially flat lower surface 114 and terminates at a concave upper surface 116. As best seen in FIG. 2, the sidewall 106 may be characterized by a first region A disposed adjacent the lower surface 114, a second region B disposed adjacent the upper surface 116, and a third region C disposed between the first and second regions A, B. The regions A, B, C provide a relatively equal division of the housing 102 into three regions about a longitudinal axis X. The sidewall 106 is bulbous and protrudes outwardly in the first region adjacent the lower surface 114 before curving inwardly at an upper end thereof and through the second and third regions B, C in a substantially uniform manner. The sidewall 106 has a substantially cylindrical shape throughout its entire length about the longitudinal axis X between the lower surface 114 and the upper surface 116.

The housing 102 is preferably ergonomic in shape to allow a user to comfortably grasp the sidewall 106 without significant hand strain. Various design considerations, including the dimensions of the product dispensing system 100, contribute to the overall ergonomic shape of the housing 102. The diameter of the housing 102 in regions A and/or C is designed to accommodate a user's hand in an ergonomic manner. In particular, a typical human hand is sized to form a C-shaped grasp having an average radius dimension of about 70 mm. If the diameter of the housing 102 is too large, a user's hand cannot grasp the housing 102 in a comfortable manner. Rather, the user's grasp is forced outwardly and causes strain on interior muscles of the hand. In contrast, if the diameter of the housing 102 is too small, a user's hand extends around the housing 102 too far and the user's fingers may overlap and/or interfere with proper holding of the housing 102.

Therefore, the dimensions of the housing 102 encourage proper grasping and use of the product dispensing system 100. The housing 102 through regions A and C includes a greatest diameter dimension of about 80 mm to about 110 mm, more preferably about 90 mm to about 100 mm, and most preferably about 95 mm. Further, the housing 102 includes a smallest diameter dimension within regions A and C of about 40 mm to about 80 mm, more preferably about 50 mm to about 65 mm, and most preferably about 55 mm. However, in other embodiments any of the regions A-C may have any size or shape to accomplish various aesthetic or functional considerations.

A gripping force of about 25 N to about 40 N is required to grasp and hold the housing 102 during use. The gripping force needed to hold the housing 102 is dependent on various factors including the weight of the product dispensing system 100, the circumference of the housing 102, the location in which the user grasps the housing 102, the friction between portions of the housing 102 and a user's hand, and various other factors. The gripping force is selected to balance the force needed to hold the housing 102 without slippage and to provide an ergonomic hand position for the user. Although an average gripping force is provided herein, it should be recognized that a greater or lesser gripping force might be required depending on the factors discussed herein.

Returning again to FIG. 2, the lower surface 114 optionally includes a plurality of feet 118 extending downwardly therefrom that are adapted to contact a support surface (not shown) such as a table, counter, or the like to position the product dispensing system 100 in an upright position. The upper surface 116 is concave and includes a circular orifice 120 disposed therethrough. A button 122 extends out of the compartment 112 and protrudes upwardly through the orifice 120. The button 122 is part of a latching mechanism that holds the front portion 108 and the rear portion 110 of the housing 112 together, the individual components of which will be explained in more detail hereinbelow.

As best seen in FIGS. 1 and 2, an elongate substantially oval opening 124 is formed in the sidewall 106 of the housing 102 of the product dispensing system 100. The opening 124 is disposed in the second region B of the sidewall 106, i.e., the upper third of the housing 102. The opening 124 extends through the entirety of the sidewall 102 and provides an outlet for fluid to be dispensed from the container 104 and may be otherwise referred to as a dispensing opening or a product spray opening. When a spray head 126 of the container 104 is depressed, product is dispersed through the opening 124 and into the surrounding atmosphere. It is preferred that the spray head 126 be disposed adjacent the opening 124, as depicted in FIG. 2, so as to allow product to escape therefrom and minimize the amount of product that may be dispensed on internal portions of the housing 102. In another embodiment, the opening 124 is provided in a different shape, such as square, circular, rectangular, and the like, and may be disposed on any portion of the housing 102. In another embodiment, the opening 124 is a communication element, or has the appearance of one, and is provided in a shape that is associated with and/or forms part of a representation or group of communication elements, as discussed hereinbelow.

Various components associated with the housing 102 of the product dispensing device 100 comprise and/or are a part of a group of communication elements. "Communication element" as used herein, relates to a means for communicating some form of information to a user. Communication elements are one or more surface variations (explained in more detail hereinbelow) that work alone or in combination with each other to provide guidance to a user as to how to set-up, hold, orient, spray, and/or otherwise use the dispensing device in its intended manner. It is envisioned that a plurality of surface variations or communication elements may provide a pattern or representation that effects this outcome. Non-limiting examples include: one or more surfaces on a dispensing device that comprise similar shapes and/or colors to form a pattern that is familiar to a person using the device, one or more surfaces that are sized to encourage a user to grasp the dispensing device in a particular location, and/or one or more surfaces that relate to each other to provide information and/or other guidance to the person using the dispensing device. As presently used, a communication element does not comprise letters, words, numbers, or other forms of known written communication.

"Intended Manner" as used herein, relates to a user operating a product in the common, ordinary course of operation as it is intended to be used. Non-limiting examples of such include grasping a dispensing device in an appropriate grasping area (i.e., with a hand not obstructing a dispensing orifice), orientating a dispensing orifice away from one's self during a spraying operation, and the like.

The housing 102 of the product dispensing device 100 preferably includes one or more surface variations that form one or more communication elements. "Surface variation" as used herein, relates to an actual surface irregularity associated with a dispensing device or gives the perception of such an irregularity. For example, if the surface irregularity is visual in nature, the surface irregularity is perceivable to a person having average vision as viewed from a distance of approximately 0.5 meters. If the surface irregularity is tactile in nature, the surface irregularity is perceptible to the touch of an individual over the age of 12 having average and functional nervous and tactile receptors. A surface variation, at a minimum, is one portion of a surface in a first state and a second portion of an adjacent surface in a state different from the first state so as to provide a contrast between the surfaces. The contrast may be communicated to the person visually, physically, or using one or more of the senses including through hearing, sight, touch, smell, and the like. The first and second portions of the surface may comprise one overall surface and/or may be discrete surfaces. Surface variations include, but are not limited to: color differences between the portions; height differences between the portions, such as one portion being recessed, protruded, or otherwise offset from the second portion; pattern differences such as one portion comprising a pattern and a second portion comprising a different pattern or no pattern at all; and textural differences such as one portion containing one material with a specified tactile feel and the second portion containing the same material with a different tactile feel or a different material with a different tactile feel.

A further embodiment of a surface variation is a material that gives the impression or illusion of a surface irregularity. For example, a dispensing device may include a surface variation in the form of a cover or wrap applied to the first and/or second surface with markings that give the perception of a surface variation visually or through tactile feedback. One or more surface variations described herein may be used alone or in combination with each other, and/or in combination with openings, and/or buttons on the dispensing device to form communication elements. Further, one or more types of surface variations may be used in combination with each other. For example, a first portion of the surface may comprise both a visual and a textural difference from a second portion. It is contemplated that any other modification to a dispensing device that is an actual or perceived surface irregularity is included in this definition.

Figure 12:
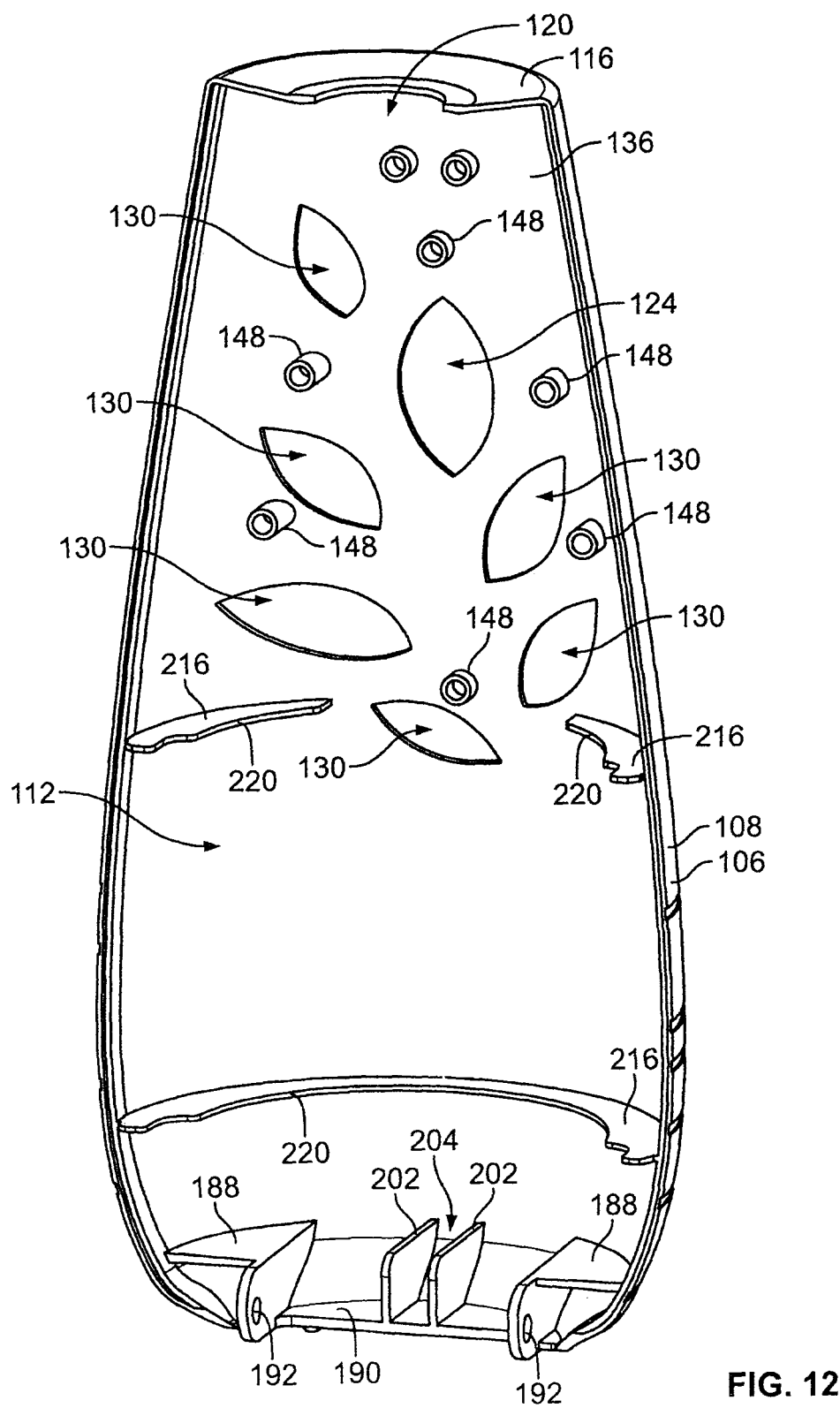
FIG. 12 is a rear side isometric view of the front portion of the housing of FIG. 3 with the plate removed therefrom.

In one embodiment depicted in FIG. 12, surface variations are provided in the form of one or more orifices 130 in combination with one or more protrusions 132. The housing 102 includes the plurality of orifices 130 extending through the sidewall 106. The orifices 130 are concentrated most predominately within the third or central region C of the housing 102. In the embodiment presently depicted, each orifice 130 is shaped like a leaf. In alternative embodiments, other decorative shapes may be utilized. In particular, orifices 130 in the shape of naturally occurring objects are preferable. The orifices 130 form a distinctive visual pattern of communication elements and are designed to receive similarly shaped protrusions 132 that extend partially therethrough. In one embodiment, the protrusions 132 are integral with the housing 102. In a different embodiment, the protrusions 132 are provided on a separate structure that is disposed within the compartment 112. In yet another embodiment, the protrusions 132 give the appearance of extending through the orifices 130, but are positioned therebelow and/or are a substantially flat and uninterrupted surface adjacent or within the orifices 130. In still another embodiment, one or more surface variations may be provided on the housing as a flat surface that contrasts with an adjacent surface. Indeed, the surface variations may be provided to the housing 102 in any form that provides a physical or visual contrast consistent with the definition provided herein.

In one embodiment, the separate structure disposed within the compartment 112 is a plate 134 (see FIGS. 5-8), which is designed to be attached to an interior surface 136 of the front portion 108 of the housing 102. The plate 134 includes a curved body 138 defined by a rear surface 140 and an opposing front surface 142. An orifice 144 extends through the body 138 that is complementary in shape to the opening 124 of the housing 102. The body 138 further includes a plurality of smaller cylindrical openings 146 that correspond to cylindrical posts 148 that extend outwardly from the interior surface 136 of the front portion 108 of the housing 102. In one embodiment, the plate 134 is held to the housing 102 when the posts 148 are disposed within the openings 146. In a different embodiment, the plate 134 is heat staked or otherwise attached to the housing 102, with or without the use of the openings 146 and posts 148. In still a different embodiment, the plate 134 is an integral piece of the housing 102. In other embodiments, the plate 134 may be attached to the housing 102 in an interference fit relationship, using slots and corresponding protrusions, using an adhesive, or via other attachment methods. The plate 134 may be permanently secured to the housing 102, partially removable and/or adjustable with respect to the housing 102, and or removable. For example, in another embodiment, the plate 134 is removable and/or interchangeable such that a user is able to adjust the visual contrast provided by the communication elements and/or omit the plate 134 all together.

The surface variations, including orifices 130 and/or protrusions 132, (otherwise referred to as communications element(s)) may be shaped in a variety of complementary and/or non-complementary manners. In one embodiment, the surface variations are shaped like an element of nature or naturally occurring object, such as branches, flowers, grass, rocks, trees, and the like. In another embodiment, the surface variations form different visual patterns by using various geometric shapes. In the embodiment depicted, six orifices 130 extend through the sidewall 106 of the housing 102 of the product dispensing system 100 and six corresponding protrusions 132 extend at least partially into the orifices 130. It is contemplated that one or more orifices 130 may be disposed in the sidewall 106 and one or more complementary protrusions 132 extend from the plate 134. In another embodiment, the protrusions 132 may be integral with the housing 102 and not disposed on a separate structure such as the plate 134. It is also contemplated that the protrusions 132 may comprise a portion of the plate 134 or other structure that is viewable through the orifices 130, regardless of whether the plate 134 or other structure is provided with portions that extend therefrom. The portion of the plate 134 or other structure constituting the protrusion 132 could be uninterrupted, planar, flat, include a depression, or only provided with a different texture, surface finish, or color than a portion of the housing 102. Indeed, the protrusion 132 may be inclusive of any structure viewable through the orifices 130. In these embodiments, the user perceives that some structure is extending through or otherwise obstructs, fully or partially, the orifice 130, which constitutes a protrusion 132 for purposes of the present disclosure.

The surface variations are designed to create a visual or physical contrast with and/or on a portion of the sidewall 106 of the housing 102. The visual contrast may be created in a variety of ways. In one embodiment depicted in FIG. 9A, the visual contrast is defined by the protrusions 132 being characterized by a first color and the sidewall 106 being characterized by a second color that is different from the first color. In one embodiment, the color difference is generated by the surface having different color materials incorporated therein. In another embodiment, the color difference is created by illuminating one or more portions of the surface variation(s). For example, one or more protrusions 132 and/or other surface variations may be illuminated using one or more lights disposed within or associated with the housing. The illumination may be decorative and/or may be used as a communication element. In particular, the illumination may indicate a status of the product dispensing system 100 such as, for example, a low battery, refill indicator, and/or current or imminent spray status.

Figure 9A:
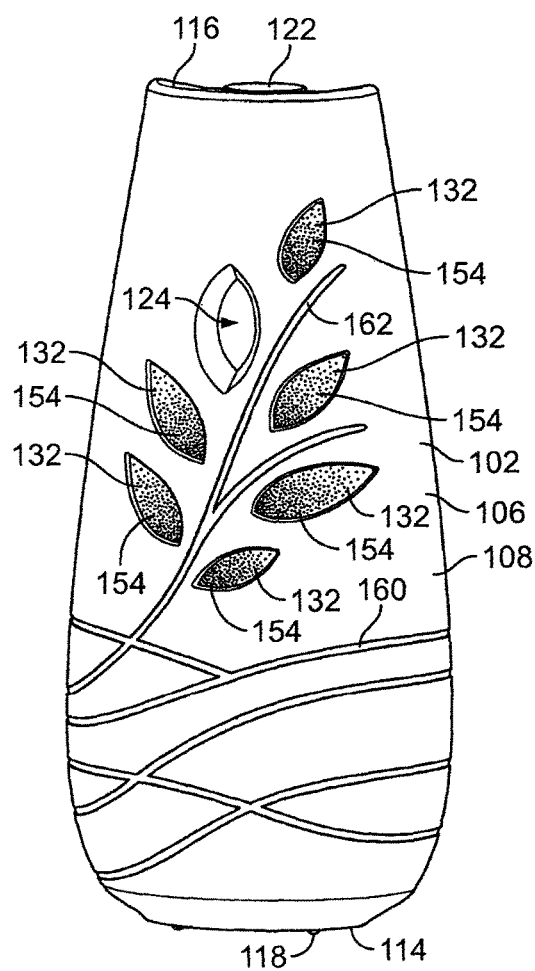
FIG. 9A is a front isometric view of the front portion of the housing and plate of FIG. 3 providing a first visual contrast.
Figure 9B:
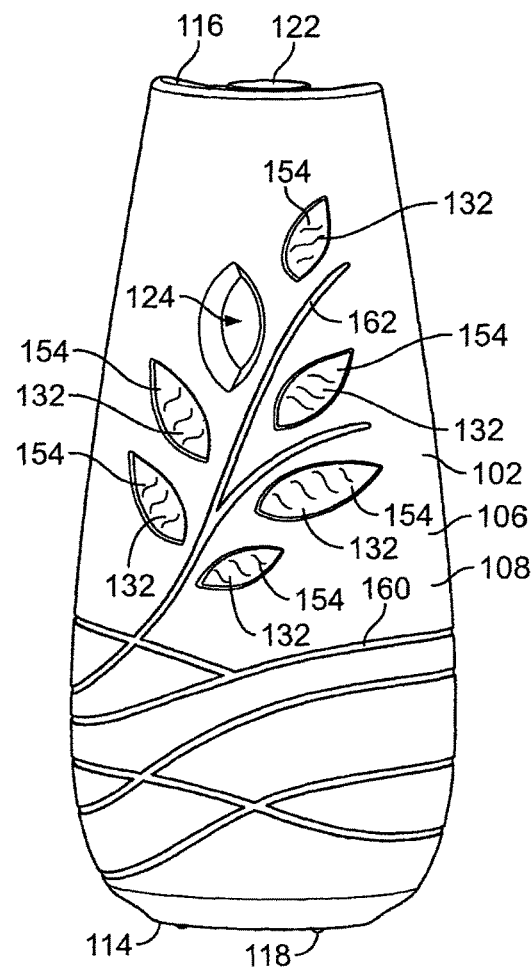
FIG. 9B is a front isometric view of the front portion of the housing and plate of FIG. 3 providing a second visual contrast.
Figure 9C:
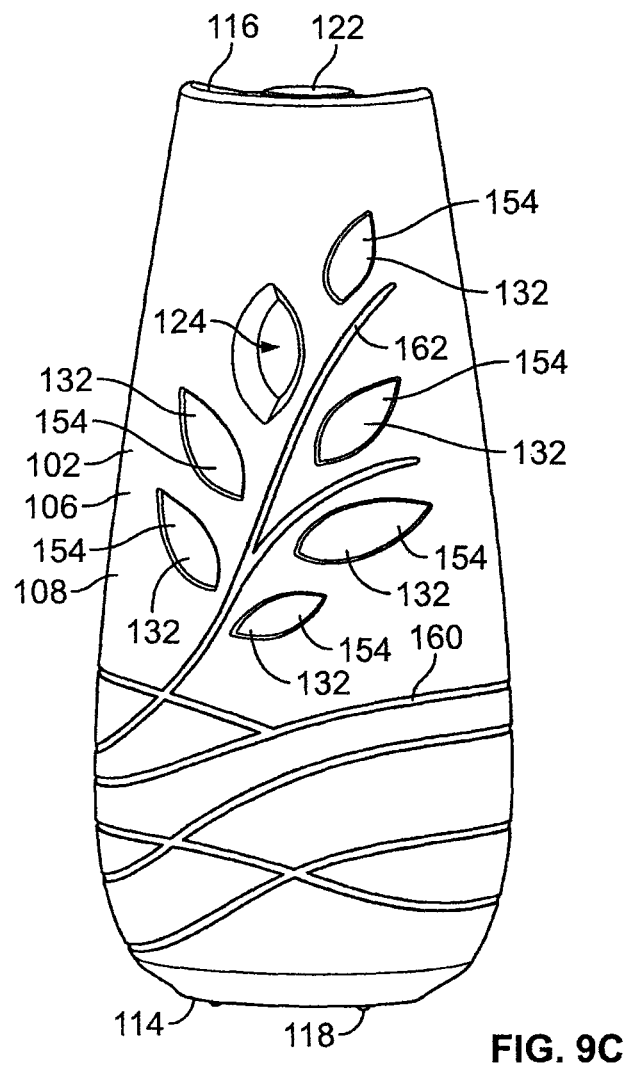
FIG. 9C is a front isometric view of the front portion of the housing and plate of FIG. 3 providing a third visual contrast.
Figure 10:
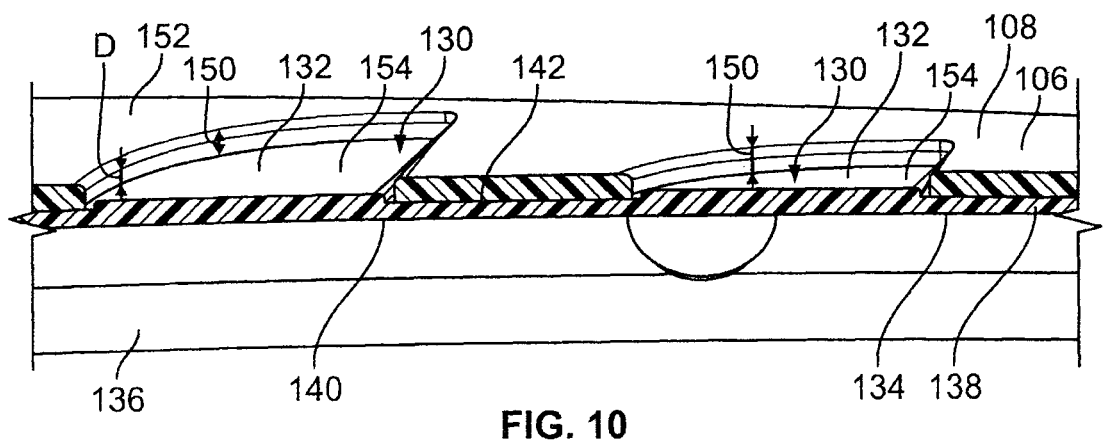
FIG. 10 is a partial cross-sectional view of the housing and plate of FIG. 3 taken generally along the line 10-10 shown in FIG. 2.

In a different embodiment shown in FIG. 9B, the visual contrast is defined by the surface variation (e.g., protrusions 132) having a surface finish different from a surface finish of the sidewall 106. For example, the sidewall 106 may have a smooth contour and the protrusions 132 may include a textured surface such as a ridge, bump, or other raised and/or depressed portion. In a different embodiment depicted in FIG. 9C, the visual contrast is defined by the protrusions 132 extending partially into the orifices 130 such that a gap 150 (see FIG. 10) is created between an outer surface 152 of the sidewall 106 and an outer surface 154 of the protrusions 132. The gap 150 is created when the outer surface 154 of the protrusion 132 is spaced from the outer surface 152 of the sidewall 106 so that the outer surfaces 152, 154, respectively, are not flush with each other. It is contemplated that one or more of these surface variations may be used in conjunction with each other, e.g., a protrusion 132 may have a color different from the color of the sidewall 106 and may include a surface irregularity.

Figure 3:
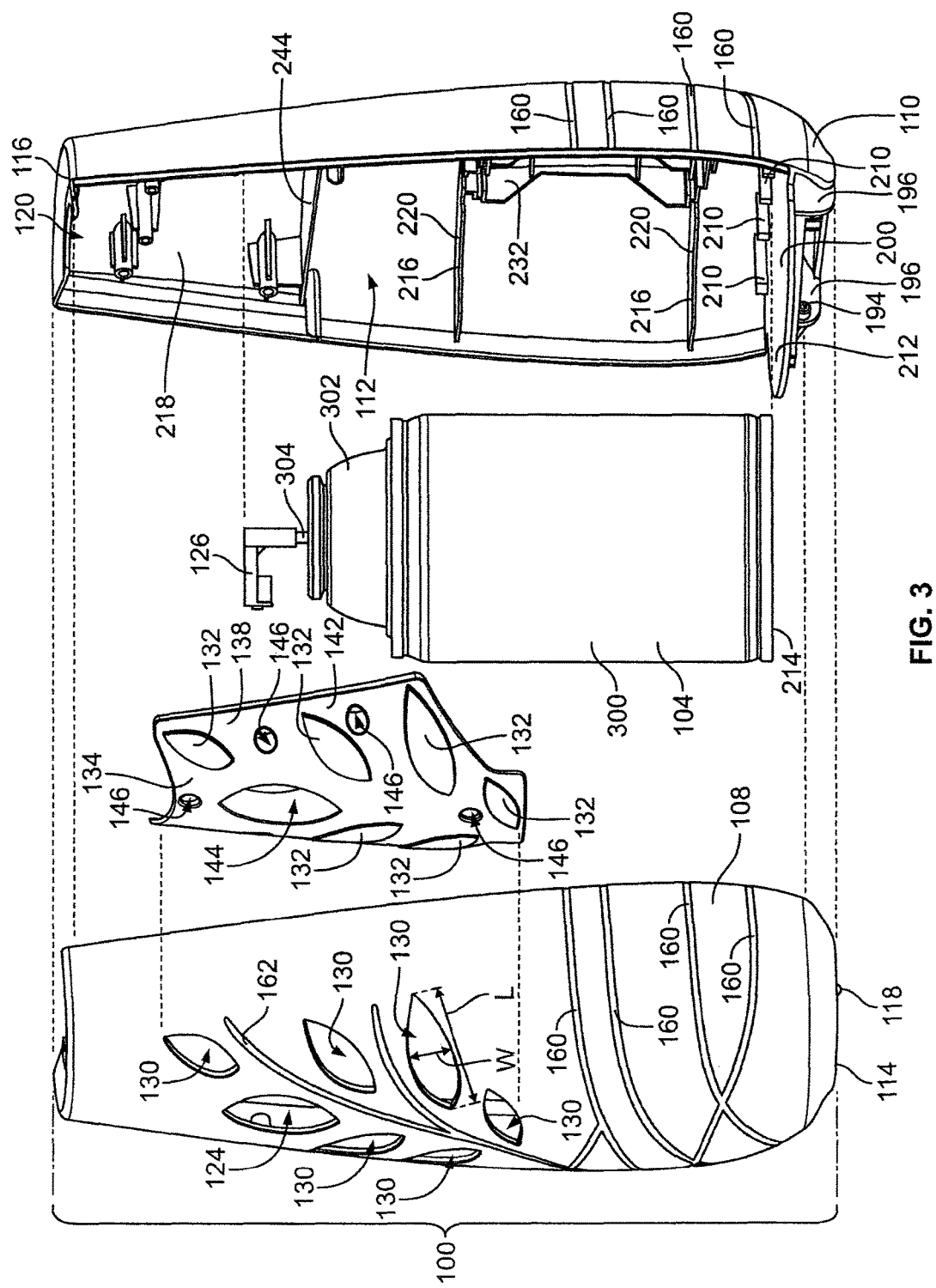
FIG. 3 is an exploded isometric view of the product dispensing system of FIG. 1 showing a front portion of the housing, a rear portion of the housing, a container, and a plate.
Figure 4:
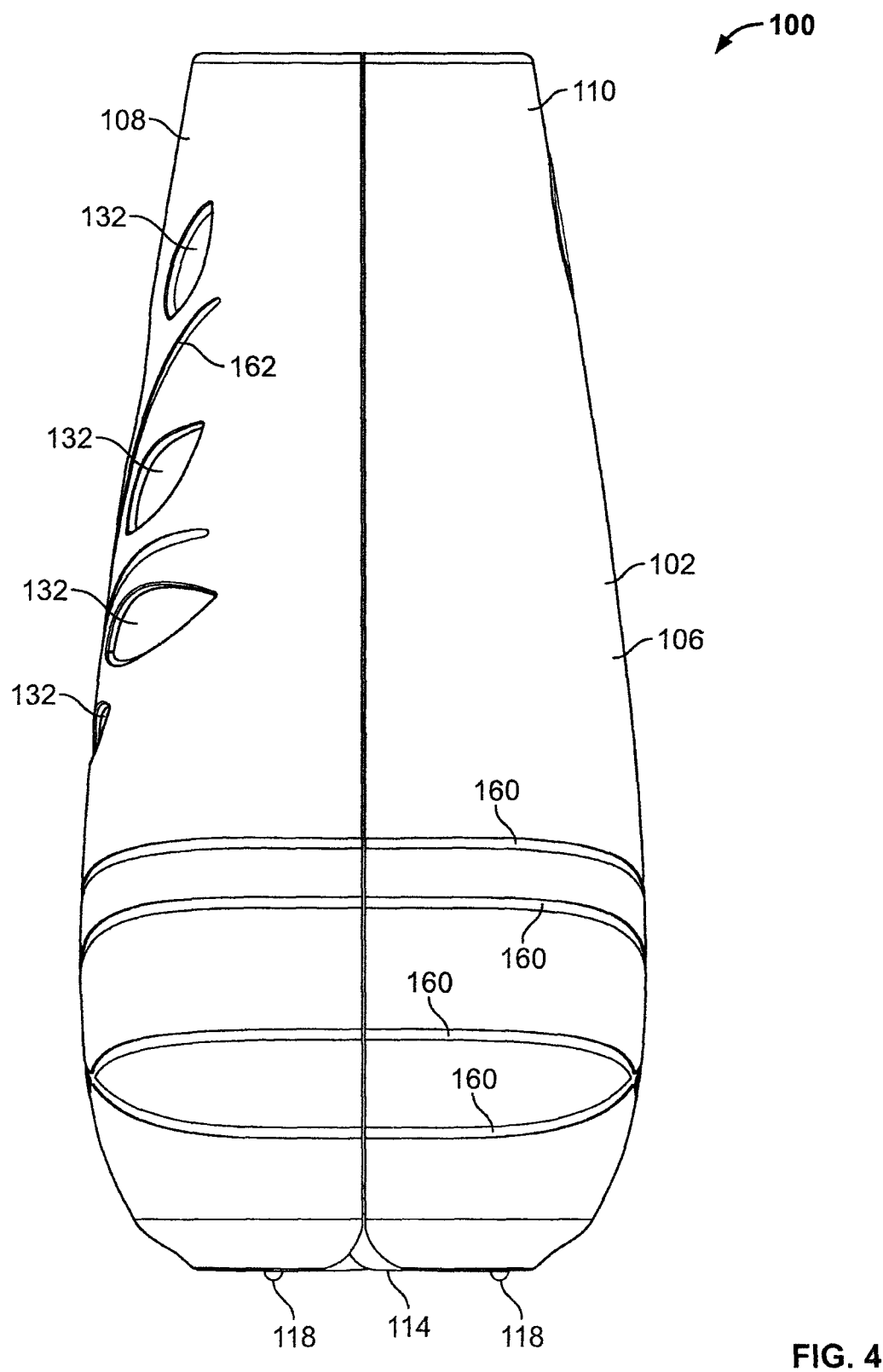
FIG. 4 is a side elevational view of the product dispensing system of FIG. 1.
Figure 6:
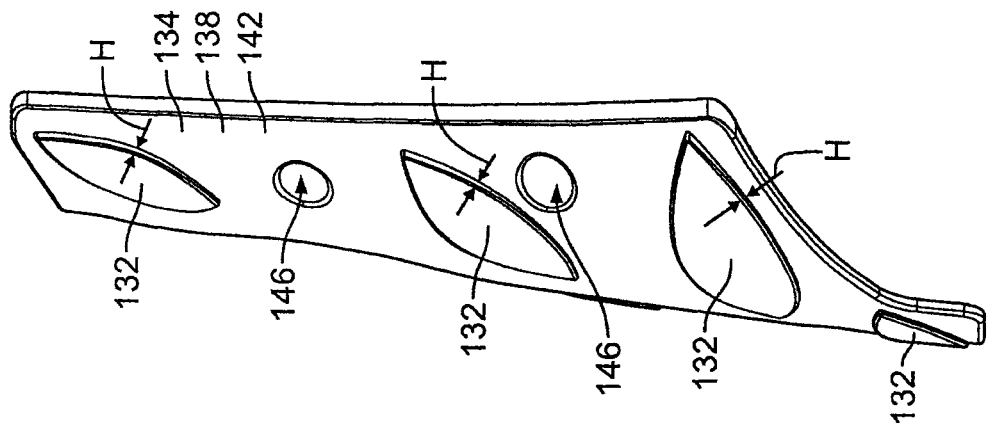
FIG. 6 is a side elevational view of the plate of FIG. 3.
Figure 5:
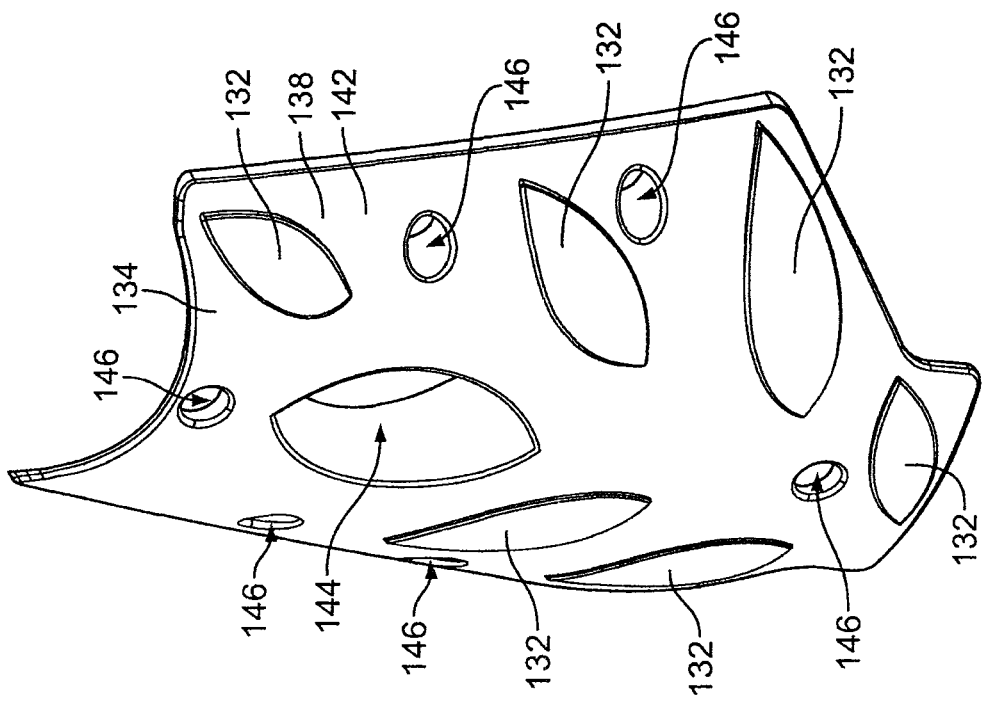
FIG. 5 is a front isometric view of the plate of FIG. 3.
Figure 8:
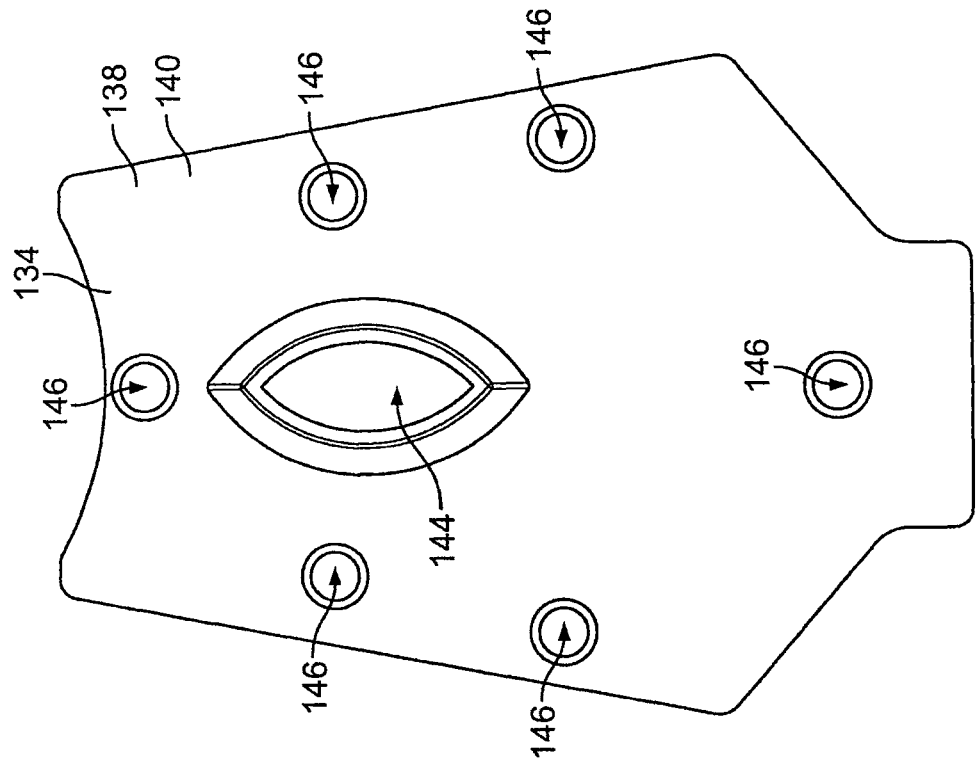
FIG. 8 is a rear elevational view of the plate of FIG. 3.

Turning to FIG. 3, the orifices 130 include a length dimension L measured between opposing ends of the orifices 130 between about 10 mm to about 75 mm, more preferably between about 30 mm to about 60 mm, and most preferably about 45 mm. The orifices 130 also include a width dimension W as measured perpendicular to the length dimension of between about 5 mm to about 50 mm, more preferably between about 20 mm to about 30 mm, and most preferably about 25 mm. The orifices 130 further include a depth dimension D (see FIG. 10) measured from an outer surface 152 of the sidewall 106 adjacent a distal end of a curved edge to an outer surface 154 of the protrusions 132 between about 0.1 mm to about 25 mm, more preferably between about 5 mm to about 15 mm, and most preferably about 10 mm.

Figure 7:
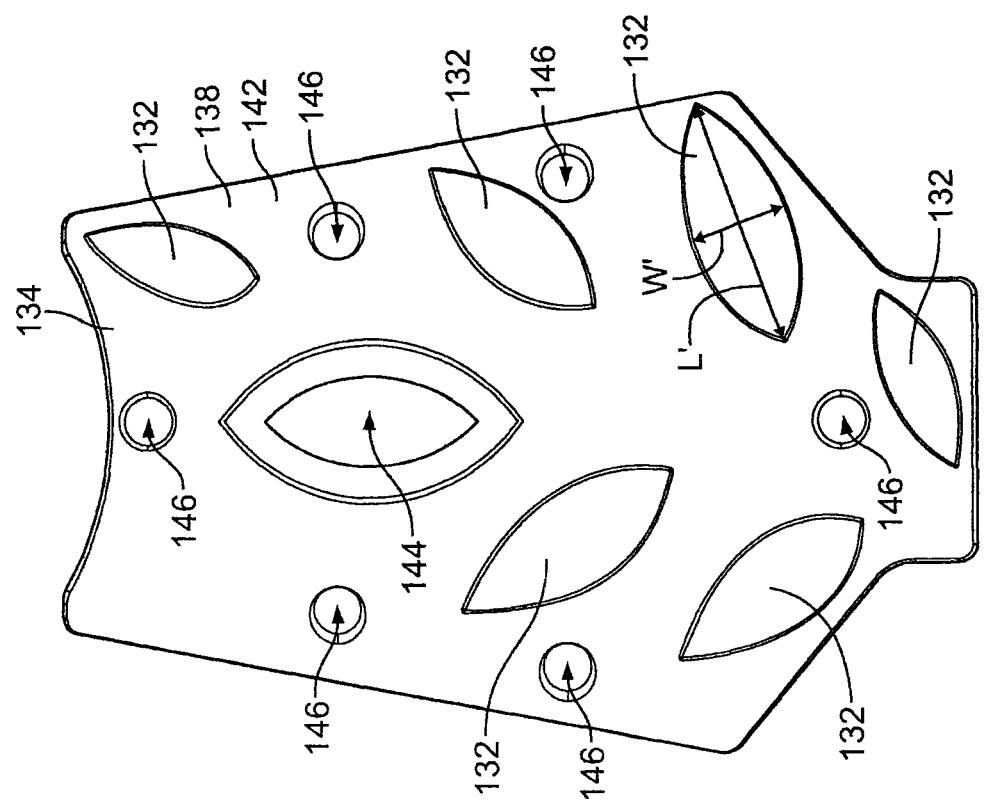
FIG. 7 is a front elevational view of the plate of FIG. 3.

Similarly, as shown in FIG. 7, the protrusions 132 include a length dimension L' measured between opposing ends of the protrusions 132 between about 10 mm to about 75 mm, more preferably between about 30 mm to about 60 mm, and most preferably about 45 mm. The protrusions 132 also include a width dimension W' as measured perpendicular to the length dimension of between about 5 mm to about 50 mm, more preferably between about 20 mm to about 30 mm, and most preferably about 45 mm. The protrusions 132 further include a height dimension H (see FIG. 6) measured from the front surface 142 of the plate 134 to the outer surface 154 of the protrusion 132 that is between about 0.1 mm to about 25 mm, more preferably between about 5 mm to about 15 mm, and most preferably about 10 mm. It should also be understood that the protrusions 132 are preferably sized to be substantially the same size or smaller than the orifices 130 to allow for effective insertion therein.

As best seen in FIGS. 1-4, the housing 102 further includes a surface variation provided in the form of a plurality of annular grooves 160 extending therearound within the first region A. The grooves 160 are provided as decorative features and may complement and/or work in conjunction with the pattern formed by other surface variations (e.g., the orifices 130) to act as a group of communication elements. In the embodiment depicted, the grooves 160 are provided as branches and further include a straightened portion 162 that extends upwardly between the orifices 130 to form a natural visual impression. Any number of grooves 160 may be optionally provided in the sidewall 106. The grooves 160 preferably provide tactile and/or visual indication of an appropriate gripping location for a user to grasp the housing 102 of the product dispensing system 100, as will be explained in more detail hereinbelow.

Figure 11:
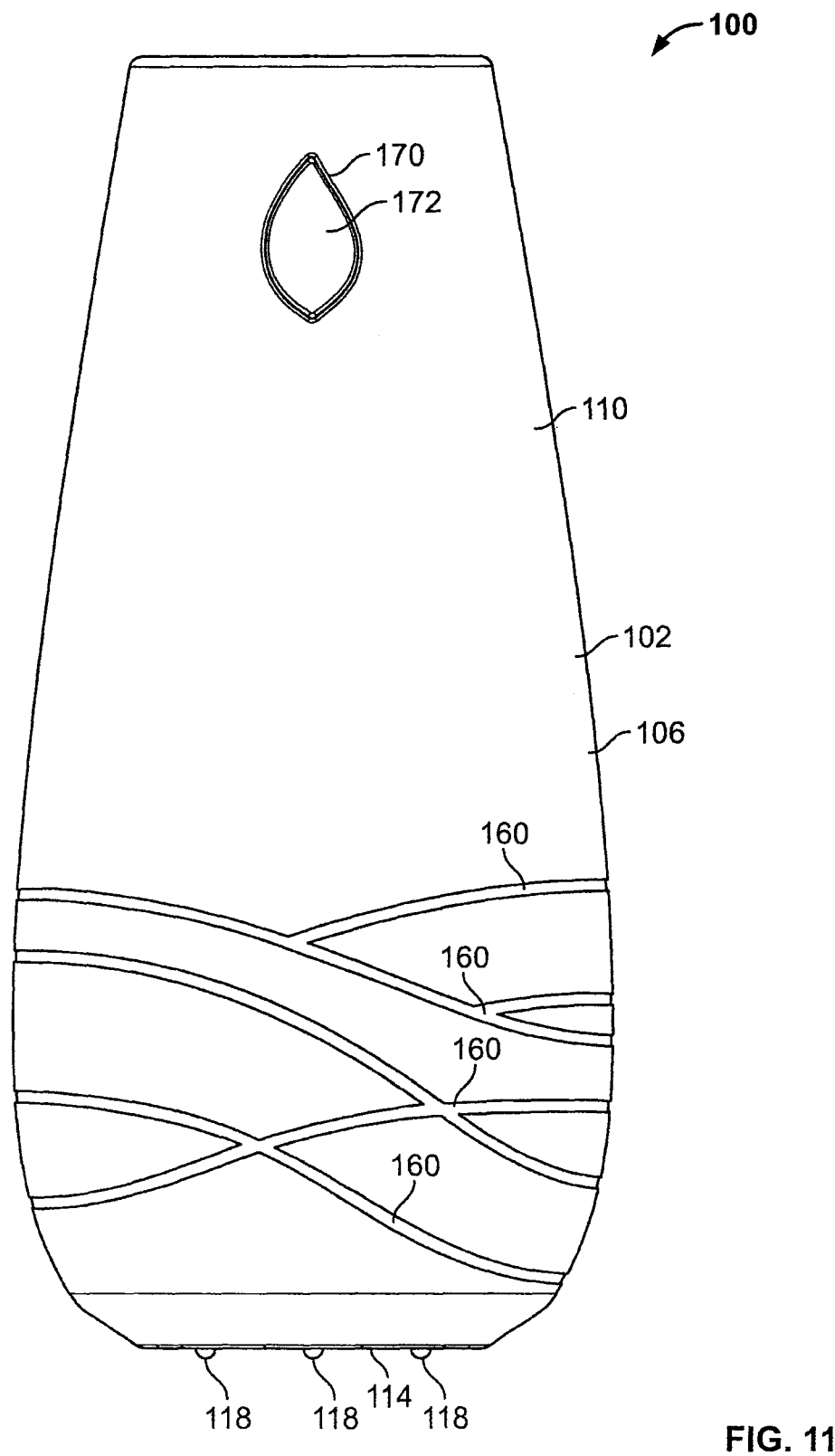
FIG. 11 is a rear elevational view of the product dispensing system of FIG. 1.

Now turning to FIG. 11, the housing 102 includes a substantially rounded tear-drop shaped hole 170 disposed in the rear portion 110 thereof adjacent the upper surface 116. The hole 170 extends through the entirety of the sidewall 106 and is designed to receive a similarly shaped manual actuation boost button 172. In one embodiment, the button 172 is preferably disposed in the second region B adjacent the upper surface 116 so as to prevent accidental actuation when a consumer grasps the product dispensing system 100. In a different embodiment, the button 172 is disposed on a side surface of the housing 102. The button 172, in conjunction with the other surface variations such as grooves 160 and/or orifices 130, may form part of the communication elements provided by the product dispensing system 100. In a different embodiment, the button 172 is omitted. The button 172 is electrically connected to a circuit board 174, which is disposed within the compartment 112 (see FIG. 17).

In one preferred embodiment, an upper end of the button 172 is spaced from the lower surface 114 of the housing 102 a distance of about 100 mm to about 140 mm along the sidewall 106. In a different or the same embodiment, the upper end of the button 172 is spaced from an upper end of a gripping region, e.g., an upper end of region A or a portion of region C, a distance of about 84 mm to about 104 mm. Placement of the button 172 in such a manner facilitates easy actuation of the button 172 by one or more fingers of a user. Further, grasping the housing 102 so that the palm of the user is adjacent the rear portion 110 of the housing 100 in regions A and/or C allows for easy manual activation of the dispensing system 100 when the button 172 is similarly positioned on the rear portion 110 and/or a side portion of the housing 102. In another embodiment, the button 172 is provided as part of the group of communication elements formed by the opening 124 and/or protrusions 132. In order for the button 172 to be considered part of the pattern formed by one or more communication elements on the housing 102, i.e. the orifices 130 and protrusions 132, the boost button 172 preferably has a similar shape to that of one or more of these communication elements on the housing 102 and/or is associated therewith in some other manner, e.g., as part of a nature scene, part of a similarly related element such as a branch or leaf, and the like.

Figure 13:
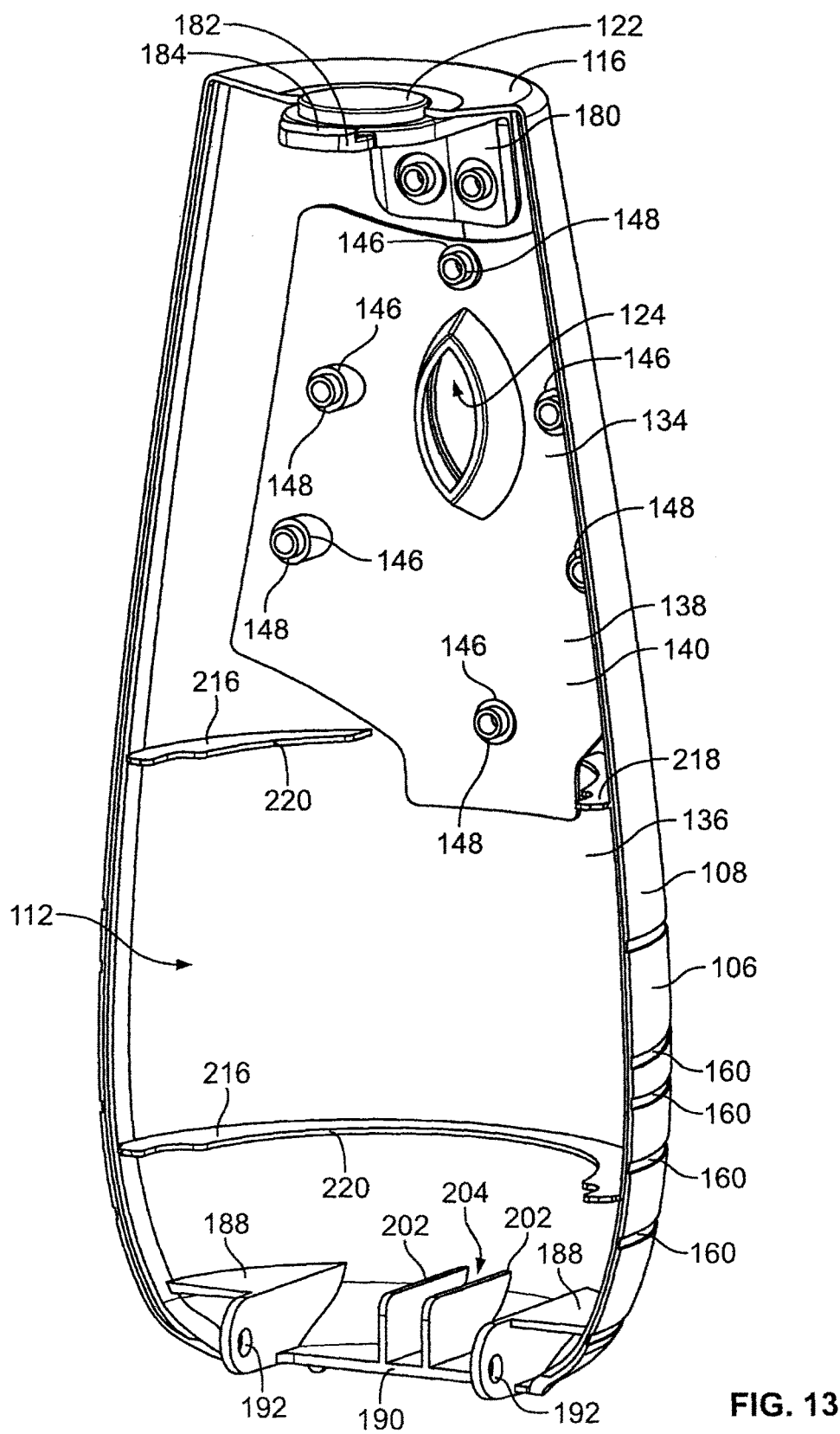
FIG. 13 is an isometric view of the front portion of the housing of FIG. 12 with the plate attached thereto.
Figure 15:
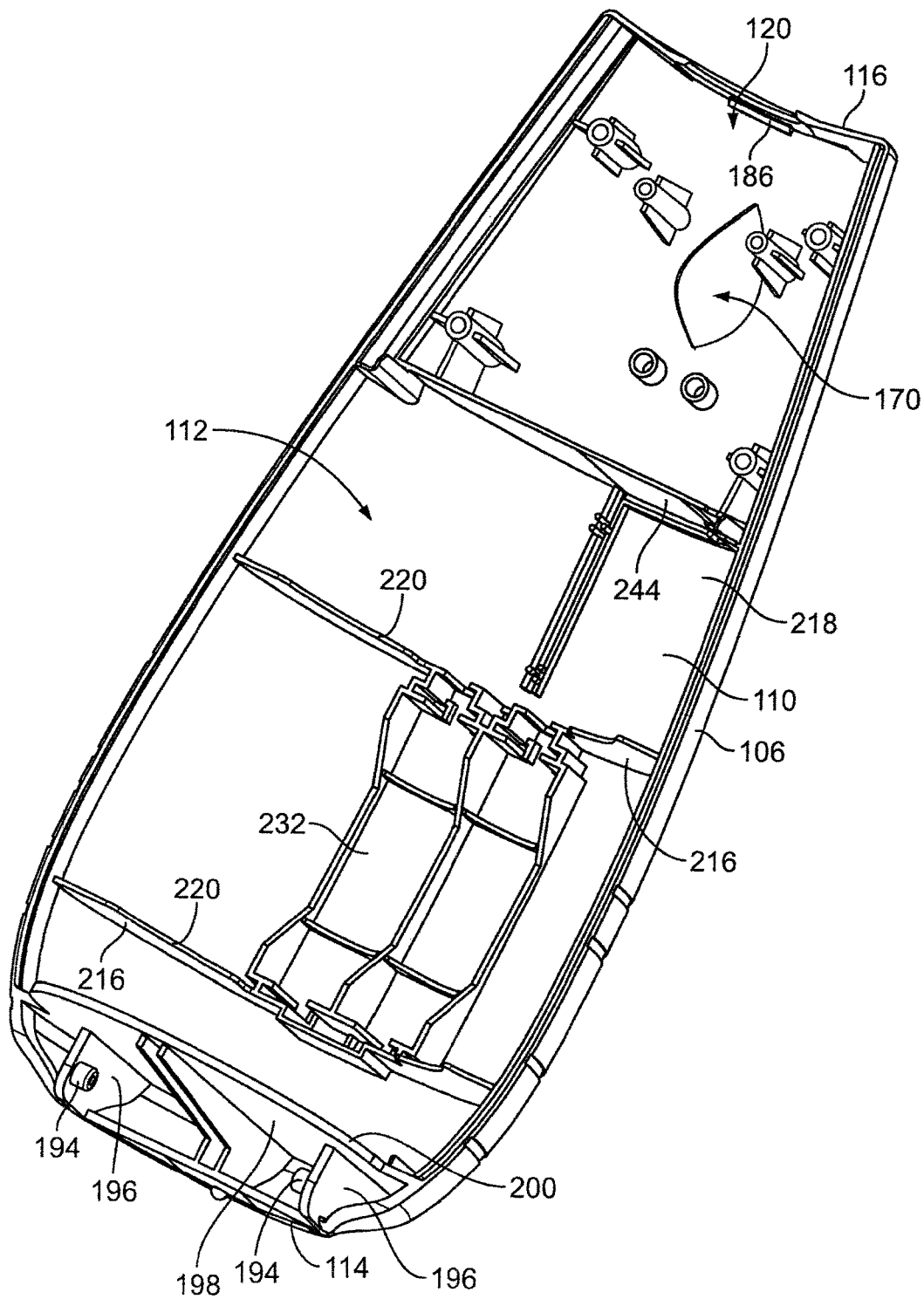
FIG. 15 is a different isometric view of the rear portion of the housing of FIG. 14.
Figure 16:
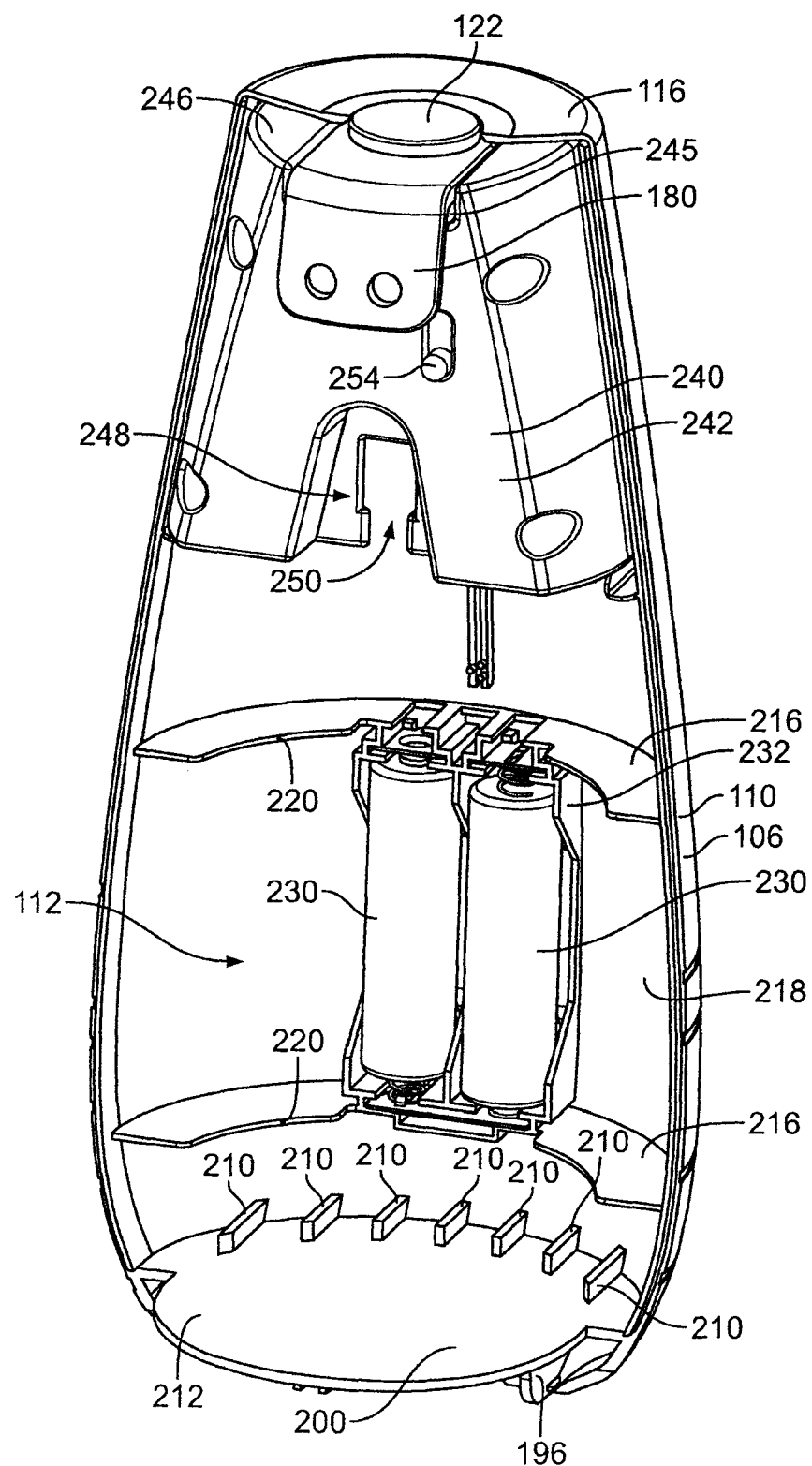
FIG. 16 is an isometric view of the rear portion of the housing of FIG. 14 further including a protective cover and batteries.

With reference to FIGS. 13 and 16, the button 122 extends inwardly into the housing 102 and is attached to the interior surface 136 of the front portion 108 of the housing 102 via a flexible L-shaped member 180. The button 122 includes a tongue 182 extending outwardly therefrom. The tongue 182 has a raised hook member 184 designed to releasably interact with a corresponding ridge 186 (see FIG. 15) disposed on the rear portion 110 of the housing 102.

As best seen in FIGS. 12 and 13, the front portion 108 of the housing 102 includes opposing brackets 188 adjacent a lower surface 190 of the compartment 112. The brackets 188 include circular holes 192 disposed therein that are adapted to receive posts 194 extending from the rear portion 110 of the housing 102. As depicted in FIG. 15, the posts 194 extend inwardly from opposing flanges 196 disposed on an underside 198 of a platform 200. When the posts 194 of the rear portion 110 are positioned within the holes 192 of the front portion 108, the front portion 108 of the housing 102 rotates about the posts 194 into an open or closed position. The button 122, in conjunction with the posts 194 and holes 192, form the latching mechanism. In particular, in the closed position the hook member 184 interacts with the ridge 186 to releasably hold the front and rear portions 108, 110 together to form a unitary housing 102. When a downward force is applied to the button 122, the hook member 184 disengages from the ridge 186 and the front portion 108 of the housing 102 may be rotated away from the rear portion 110 of the housing 102. In this way, a user may access the compartment 112 for a variety of functions that will be explained in more detail below.

With reference to FIGS. 12 and 13, in the closed position a portion of the platform 200 rests on two elongate ribs 202 that extend upwardly from the lower surface 190 of the housing 102. The ribs 202 are disposed side-by-side and include a gap 204 therebetween. The ribs 202 are spaced interiorly of the brackets 188.

Figure 14:
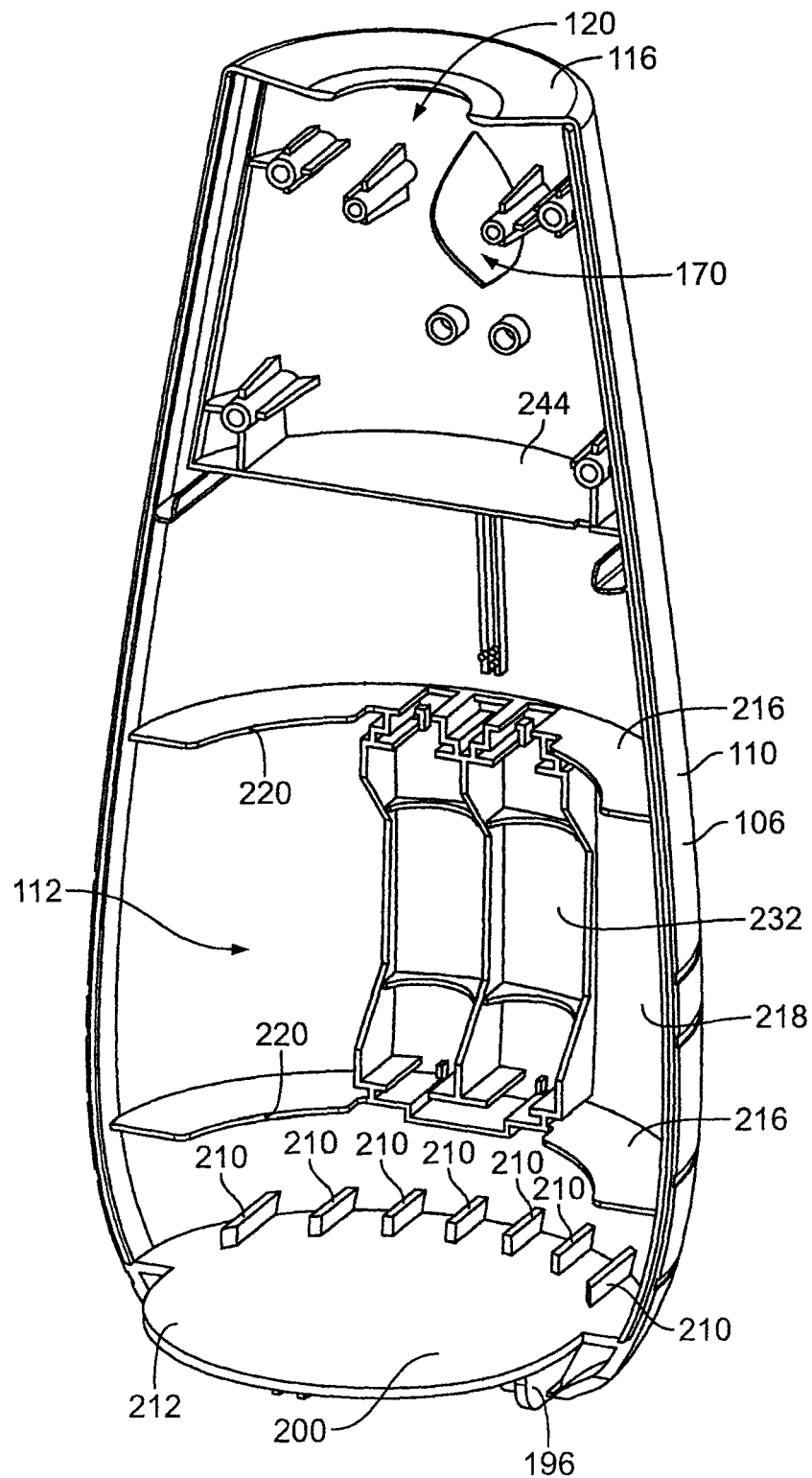
FIG. 14 is a front side isometric view of the rear portion of the housing of FIG. 3.

Turning to FIGS. 14-16, the platform 200 includes a plurality of rectilinear members 210 circumscribing an upper surface 212 thereof. The rectilinear members 210 are oriented to act as a retention mechanism when the container 106 is disposed on the platform 200. A base 214 of the container 106 contacts the rectilinear members 210 when the container 106 is inserted into the housing 102. A plurality of stabilizing ribs 216 extend from and circumscribe the interior surface 136 of the front portion 108 (see FIGS. 12 and 13) and an interior surface 218 of the rear portion 110 (see FIGS. 14-16) of the housing 102. The stabilizing ribs 216 include outer edges 220 that correspond to the contour of the container 106 and assist in retaining the container 106 in an upright position.

FIG. 16 depicts a power source of the product dispensing system 100, which in the present embodiment is provided in the form of batteries 230. The batteries 230 are disposed within a retaining structure 232 that extends inwardly from the rear portion 110 of the housing 102. Although batteries 230 are depicted, it is contemplated that any known power sources may be utilized, e.g., the power source may be a standard wall outlet accessed by a plug on the housing 102 or a cord and plug extending from the housing 102 (not shown).

Now turning to FIGS. 14-19, various components related to the operation of the product dispensing system 100 will be described with greater particularity. The components are enclosed within a protective cover 240 (see FIG. 16). The protective cover 240 includes a substantially V-shaped body 242 that corresponds to the contour of the sidewall 106 of the housing 102 and terminates at a horizontal sidewall 244 (see FIG. 15). The sidewall 244 extends across the rear portion 110 of the housing 102 and provides structural support to the components within the protective cover 240. The L-shaped member 180 of the button 122 rests in a recess 245 (see FIG. 16) in an upper surface 246 of the protective cover 240. The protective cover 240 further includes a U-shaped cutout 248 disposed adjacent the horizontal sidewall 244 and an opening 250 therein. The opening 250 is preferably sized to receive the spray head 126 of the container 106.

Figure 17:
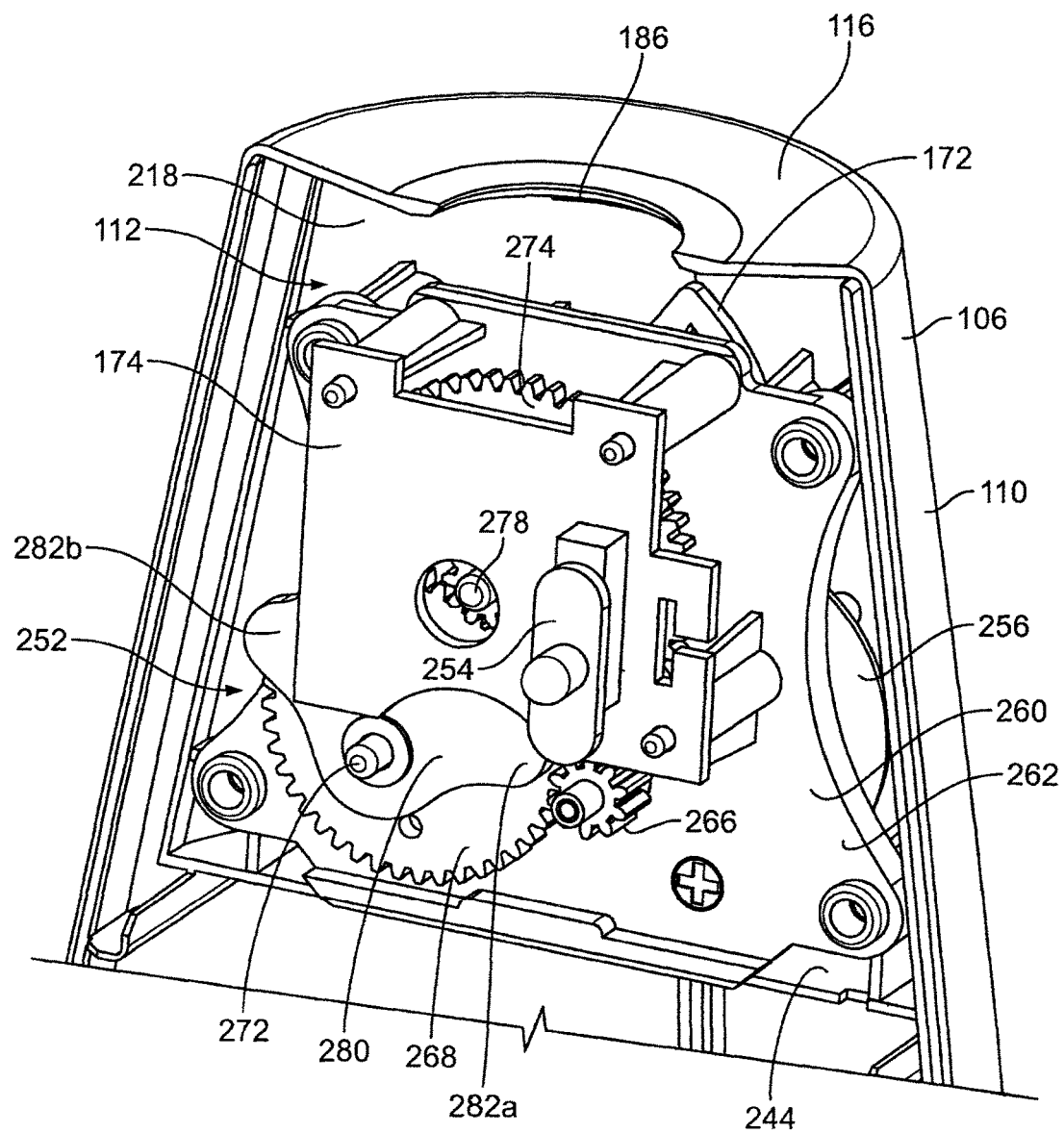
FIG. 17 is a partial front isometric view of the rear portion of the housing of FIG. 16 with the protective cover removed for clarity and showing a camming mechanism and circuit.

As best seen in FIG. 17, the circuit board 174 and an actuation mechanism are disposed within the protective cover 240. In the present embodiment, the actuation mechanism comprises a camming mechanism 252. The camming mechanism 252 is electrically connected to the circuit board 174 and associated microcontroller, which receives power from the batteries 230. The circuit board 174 is further electrically connected to the manual actuation button 172 and a switch 254.

With reference to FIG. 16, the switch 254 extends through an opening in the protective cover 240 to provide easy access thereto. The circuit board 174 translates the switch mode that is selected by the user into the appropriate actuation sequence of the camming mechanism 252. In one embodiment, the switch 254 includes a variety of timing sequences and/or operating conditions that may be selected by the user. For example, one such timing sequence allows the user to set a preset dispensing interval so the product dispensing device 100 dispenses automatically at specified intervals. The intervals may be preset for any amount of time, but one such preset sequence allows the user to select between an "OFF" function and 9, 18, and 36 minute intervals.

Figure 18:
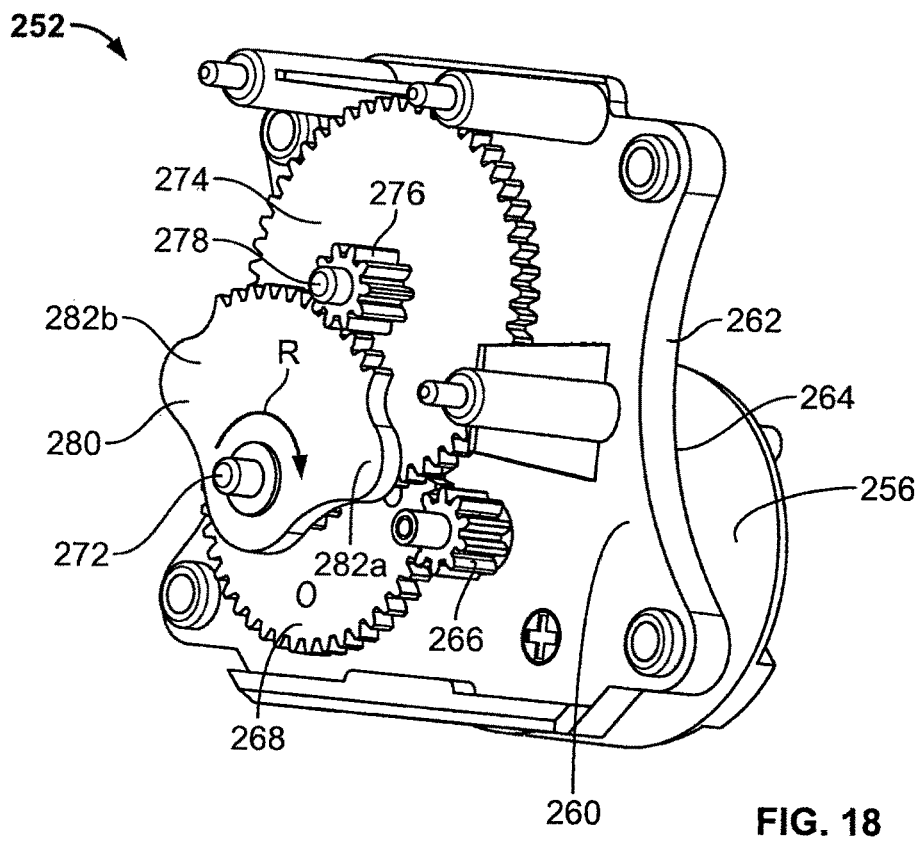
FIG. 18 is a front left side isometric view of the camming mechanism of FIG. 17.
Figure 19:
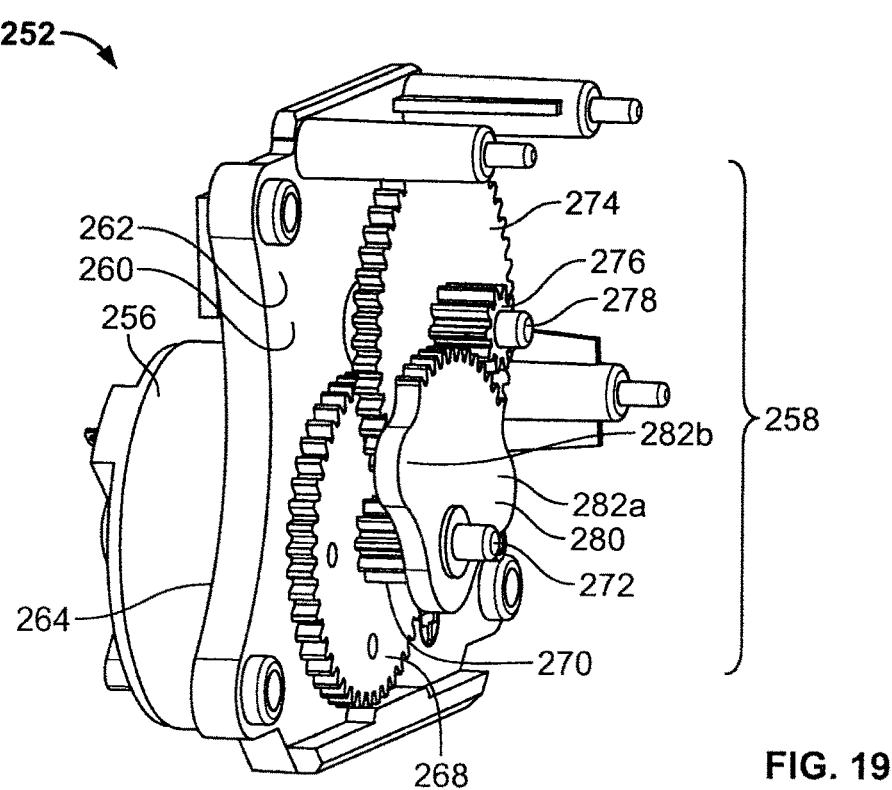
FIG. 19 is a front right side isometric view of the camming mechanism of FIG. 17.

Now turning to FIGS. 17-19, the camming mechanism 252 is shown within an upper portion of the compartment 112. The camming mechanism 252 is provided in mechanical association with a drive motor 256 and a reduction gear train 258. The gear train 258 is mounted on a front side 260 of a gear plate 262 and the drive motor 256 is mounted on a rear side 264 of the gear plate 262.

The drive motor 256 includes a first pinion gear 266, which meshes with a drive gear 268. The drive gear 268 includes a second pinion gear 270 (see FIG. 19) that is rotatable about an axle 272. The second pinion gear 270 of the drive gear 268 meshes with an idler gear 274. The idler gear 274 includes a third pinion 276 that is rotatable about an axle 278. The third pinion gear 276 of the idler gear 274 meshes with a lever gear 280. The drive, idler, and lever gears 268, 274, 280, respectively, are disposed on the gear plate 262. The axles 272 and 278 are molded extrusions extending from the gear plate 262.

The lever gear 280 includes rounded actuating arms 282a, 282b protruding outwardly from opposing sides thereof. When the lever gear 280 is rotated by the gear train 258 and the drive motor 256 in a clockwise direction as shown by arrow R (see FIG. 18), the actuating arm 282a of the lever gear 280 is rotated downwardly and contacts the spray head 126. Conversely, when the lever gear 280 is rotated in a counter-clockwise direction, the rounded arm 282 is rotated upwardly toward a pre-actuation position.

The lever gear 280 is rotated a pre-specified distance to a discharge position such that a valve stem 304 of the container is depressed and the valve assembly is opened, thereby allowing discharge of product through the spray head 126. The particular rotational distance is selected to coincide with a partial or full depression of the valve stem 304. Fully depressing the valve stem 304 releases either a full metered discharge or a continuous discharge of the container contents, while partially depressing the valve stem 304 results in a partial metered or partial continuous discharge of the container contents. Preferably, although not necessarily, the actuating arm 282a is held in the discharge position for a length of time (referred to hereinafter as a "spraying period"). The duration of the spraying period could range anywhere from a fraction of a second to one or more seconds. At the end of the spraying period, the drive motor 256 is deenergized and the actuating arm 282a returns to the pre-actuation position and terminates further spraying. In one embodiment, the drive motor 256 is activated to drive in a counter-clockwise direction to assist in returning the lever gear 280 to a pre-operative position.

Referring again to FIG. 3, the product dispensing system 100 is designed to be used with a container 106 having the spray head 126. In one embodiment, the container 106 comprises a substantially cylindrical body 300 extending from the base 214. The body 300 includes a mounting cup 302 crimped to an upper end thereof. A valve stem 304 extends upwardly from the mounting cup 302. The valve stem 304 is fluidly connected to a valve body (not shown) and a valve spring (not shown) disposed within the container 106. The spray head 126 is disposed on a distal end of the valve stem 304.

In use, the product dispensing system 100 is adapted to release a product from the container 106 upon the occurrence of a particular condition. The condition could be the manual activation of the camming mechanism 252 via the button 172 or the automatic activation of the camming mechanism 252 in response to an electrical signal from the switch 254. The product discharged may be a fragrance or insecticide disposed within a carrier liquid, a deodorizing liquid, or the like. The product may also comprise other actives, such as sanitizers, air fresheners, odor eliminators, mold or mildew inhibitors, insect repellents, and/or the like, and/or that have aromatherapeutic properties. The product alternatively comprises any solid, liquid, or gas known to those skilled in the art that may be dispensed from a container. It is also contemplated that the container may contain any type of pressurized or non-pressurized product and/or mixtures thereof. The product dispensing system 100 is therefore adapted to dispense any number of different products.

During actuation, the product dispensing system 100 includes a camming mechanism 252 having an actuation force between about 1.5 Kg/min to about 2.8 Kg/min, more preferably between about 1.8 Kg/min to about 2.5 Kg/min, and most preferably about 2 Kg/min, as determined when the camming mechanism 252 has a power supply of about 3.2 V. The activation force ensures that the actuating arm 282a has enough downward force to depress the spray head 126 to release the desired amount of product. During actuation, movement of the spray head 126 may be characterized by a vertical actuation stroke. The spray head 126 preferably has a vertical actuation stroke of between about 4 mm to about 12 mm, more preferably about 6 mm to about 10 mm, and most preferably about 8 mm.

The product dispensing system 100 may be further characterized by the duration of the spray function, i.e., the time it takes to dispense product from the spray head 126. Product is dispensed from the spray head 126 at a time of between about 0.1 seconds to about 2 seconds, more preferably between about 0.8 seconds to about 1.3 seconds, and most preferably about 1 second. In one embodiment, approximately 90 microliters of product is dispensed during the spray function. In a different embodiment more than 90 microliters of product is dispensed during the spray function. In yet a different embodiment, less than 90 microliters of product is dispensed during the spray function.

The product dispensing system 100 is also aesthetically pleasing to users and has numerous features that assist a user in proper operation of the system. For example, the product dispensing system 100 is aesthetically pleasing due to the slender nature of the housing 102 and the pattern of communication elements (i.e., surface variations) incorporated therein. The communication elements of the product dispensing system 100 may also serve other useful purposes, such as instructing the user as to proper hand position before and during actuation, assisting a user's gripping of the system through frictional forces, assisting the user's gripping of the system by placement of one or more fingers within one or more communication elements, and instructing a user on proper system positioning and/or orientation without the need for intrusive instructions.

One particular feature of the product dispensing system 100 that assists a user in effective use thereof is the positioning of the manual actuation button 172 on the rear portion or side portion of the housing 102 away from a similar side as the opening 124 that spray is emitted through. Such a positioning of the button 172 has the advantage of minimizing accidental actuation of the button 172 when a user grasps the housing 102.

The communication elements further provide a guiding feature so a user understands how to grasp the housing 102 in an orientation that allows a user to immediately discern the location of the opening 124 and position their hand accordingly to effectively grasp the housing 102. Further, such an orienting function also assists the user in avoiding any contact with the housing 102 adjacent the opening 124 to avoid product being dispensed onto their hand and/or any residual product that may be on the housing 102 adjacent the opening 124.

The communication elements and/or portions of the housing 102 further provide a textured surface that the user grasps to assist the user in retaining the housing 102 in a preferred orientation. In particular, the grooves 160 circumscribe the housing 102 in region A, which is the preferred area for hand placement when a user grasps the product dispensing system 100. The depth of the grooves 160 provide a textured contrast with the adjacent surface of the housing 102 so a user's hand can easily discern the proper hand placement without visually inspecting the dispensing system 100. The grooves 160 further assist a user in holding the product dispensing system 100 due to friction created when portions of a user's fingers are provided adjacent the grooves 160. Further, orifices 130 and/or protrusions 132 within regions A and/or C may also assist a user in gripping the housing 102 in a similar manner as discussed above. Indeed, the orifices 130 and/or protrusions 132 may have the added benefit of allowing a user to insert one or more fingers into one of the orifices or protrusions to gain a better grip of the housing.

A user is further assisted in grasping the product dispensing system 100 by the dimensions of the housing 102. The tapering cross-sectional width of the housing provides an ergonomic gripping surface that conforms to the contour of a user's palm and/or fingers when gripping the housing 102. The circumference of the housing 102 is selected to be ergonomic and comfortable for the majority of adult hands that will grasp the product dispensing system 100. It is also contemplated that the housing may be provided with a uniformly cylindrical housing, a housing that tapers outwardly from a lower end to an upper end, or a housing that has varying tapering portions. Indeed, such variations may also be provided in non-cylindrical housings as well.

The communication elements further provide a guiding function due to the pattern formed thereby. For example, in the embodiment depicted, the grooves 160 give the impression of roots at the base of a plant, with a main branch (i.e., straightened portion 162) extending therefrom. The orifices 130/protrusions 132 form leaves extending from the branch and roots. The pattern formed by the communication elements invokes a familiar object (i.e., a plant) to the user. In turn, the familiar object guides the user to position their hand in a similar way around the dispensing system 100 in the same way that a user would grasp a plant. Indeed, a user would intuitively grasp a plant around its base as opposed to grasping the leaves or branches. Although the communication elements are depicted in the form of a plant, it is envisioned that other representations using the same methodology could be incorporated into the product dispensing system 100 to evoke familiarity with respect to proper hand placement.

For example, other plant shapes with roots, stems, and/or leaves could be utilized. In one embodiment, a cactus is portrayed, in which the represented prickly portions may suggest to a user to avoid that area. In a different embodiment, the housing takes on the characteristic of a natural setting of nature, which includes portions that intuitively suggest avoidance by a user and other areas that suggest a safe, comforting, or preferable placement of a user's hand based on impressions of such a setting in nature. Other natural objects such as living creatures may be represented. Further, inanimate naturally occurring objects such as rocks may be utilized. Indeed, other non-natural representations may be used insofar that a portion of the representation suggest that a user should grasp it and another different portion of the representation suggests that the user should avoid grasping it.

A further advantage of the product dispensing system 100 is the incorporation of the opening 124 into the communication elements described herein. The shape of the opening 124 has a relationship to the pattern of the other communication elements. For example, in the embodiment depicted, the opening 124 is provided in the shape of a leaf. The shape of the opening 124 is substantially similar to the other leaves (i.e., orifices 130/protrusions 132), which allows the opening 124 to blend in with the other communication elements. It is envisioned that the shape of the opening 124 could be other shapes and sizes consistent with the disclosure herein.

Although specific numbers of surface variations such as protrusions/orifices/grooves have been described with respect to the embodiments presented herein, it is contemplated that any number, shape, and size of surface variations can be utilized. Further, reference has been made throughout to multiple surface variations that do not necessarily need to be equidistant, symmetrical or similar in size and/or shape.

Any of the embodiments described herein may be modified to include any of the structures or methodologies disclosed in connection with different embodiments. Further, the present disclosure is not limited to aerosol containers of the type specifically shown. Still further, the product dispensing system may be modified to work with any type of aerosol or non-aerosol container.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A product dispensing system, comprising:
a housing having a sidewall with at least one communication element provided thereon, the sidewall comprising at least a first side and a second different side coupled to the first side, the first side and the second side each configured to extend below a bottom of a container coupled to the housing;
a dispensing opening provided inwardly from a periphery of the first side of the sidewall;
a plate coupled to an interior surface of the sidewall; and
a switch that controls an automatic dispensing sequence,
wherein the at least one communication element is configured to provide guidance as to how to set-up, hold, orient, spray, or otherwise use the product dispensing system,
wherein the at least one communication element includes at least one orifice extending through the sidewall and at least one protrusion that extends from the plate and at least partially through the at least one orifice, and
wherein the second different side of the sidewall is configured to accommodate a user's hand in an ergonomic manner.

2. The product dispensing system of claim 1, wherein the at least one orifice is formed within the first side.

3. The product dispensing system of claim 1, wherein the at least one protrusion is integrally formed with the plate.

4. The product dispensing system of claim 1, wherein the at least one communication element is provided on the first side of the sidewall and adjacent the dispensing opening.

5. The product dispensing system of claim 1, wherein the at least one communication element is provided on the second side of the sidewall.

6. The product dispensing system of claim 1, wherein the at least one communication element is provided at least partially on portions of both the first and second sides of the sidewall.

7. A product dispensing system, comprising:
a housing having a sidewall extending between a lower surface and an upper surface with at least one communication element thereon, the sidewall including a first side portion coupled to a second side portion that together form a compartment for a container;
a plate arranged within the compartment; and
a dispensing opening formed inwardly from a periphery of and completely within the first side portion of the sidewall,
wherein the housing is configured to extend below a bottom of the container coupled to the housing,
wherein the at least one communication element includes at least one orifice extending through the sidewall and at least one protrusion that extends from the plate and at least partially through the at least one orifice,
wherein the dispensing opening is provided within an upper region of the housing, and
wherein the at least one communication element assists the user in avoiding contact with the housing adjacent the dispensing opening to avoid product being dispensed onto the user's hand or to avoid any residual product on the housing adjacent the dispensing opening.

8. The product dispensing system of claim 7, wherein the dispensing opening is provided within an upper ⅓ of the housing.

9. The product dispensing system of claim 7, wherein the first side portion opposes the second side portion.

10. The product dispensing system of claim 7, wherein the sidewall has a greatest diameter dimension of between about 60 mm to about 100 mm in the upper region of the housing.

11. The product dispensing system of claim 7, wherein the sidewall has a greatest diameter dimension of between about 80 mm to 110 mm.

12. A product dispensing system, comprising:
a housing having a sidewall extending between a lower surface and an upper surface with a plurality of communication elements thereon, the sidewall including a first side portion coupled to an opposing second side portion that together form a compartment for a container;
a plate arranged within the compartment; and
a dispensing orifice formed inwardly from a periphery of and completely within the first side portion of the sidewall;
wherein the dispensing orifice has a shape similar to at least one of the plurality of communication elements,
wherein at least one of the plurality of communication elements includes at least one orifice extending through the sidewall and at least one protrusion that extends from the plate and at least partially through the at least one orifice, and
wherein the dispensing orifice is disposed between at least two of the plurality of communication elements on the first side portion.

13. The product dispensing device of claim 12, wherein the at least one communication element is configured to provide guidance as to how to set-up, hold, orient, spray, or otherwise use the product dispensing system.

14. The product dispensing system of claim 12, wherein a plurality of communication elements are provided that have a shape, which is similar to the dispensing orifice.

15. The product dispensing system of claim 14, wherein the similar shapes of the dispensing orifice and the plurality of communication elements comprise a leaf shape.

16. The product dispensing system of claim 12, wherein the plurality of communication elements are a different size than the dispensing orifice.

17. The product dispensing system of claim 12, wherein the shape of the plurality of communication elements and the shape of the dispensing orifice form a pattern, and wherein the shapes are not identical.

18. The product dispensing system of claim 12, wherein the sidewall protrudes outwardly in a first region adjacent the lower surface before curving inwardly at an upper end of the first region and through a second region and a third region, the third region adjacent the upper surface, and the second region between the first region and the third region.

* * * * *